(12) United States Patent
Cao

(10) Patent No.: US 11,969,346 B2
(45) Date of Patent: Apr. 30, 2024

(54) HEART VALVE COAPTATION DEVICE

(71) Applicant: Edwards Lifesciences Corporation, Irvine, CA (US)

(72) Inventor: Hengchu Cao, Irvine, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 326 days.

(21) Appl. No.: 17/163,215

(22) Filed: Jan. 29, 2021

(65) Prior Publication Data

US 2021/0145582 A1 May 20, 2021

Related U.S. Application Data

(63) Continuation of application No. 15/843,995, filed on Dec. 15, 2017, now Pat. No. 10,905,554.
(Continued)

(51) Int. Cl.
*A61F 2/24* (2006.01)
*A61B 17/122* (2006.01)
(Continued)

(52) U.S. Cl.
CPC ........ *A61F 2/2463* (2013.01); *A61B 17/1227* (2013.01); *A61B 2017/00243* (2013.01); *A61B 17/0487* (2013.01); *A61B 2017/0496* (2013.01); *A61B 17/1285* (2013.01); *A61F 2/0077* (2013.01); *A61F 2/2466* (2013.01); 
(Continued)

(58) Field of Classification Search
CPC .... A61F 2/2463; A61F 2/0077; A61F 2/2466; A61F 2210/0014; A61F 2220/0016; A61F 2220/0025; A61F 2220/0058; A61B 17/1227
See application file for complete search history.

(56) References Cited

U.S. PATENT DOCUMENTS 3,874,388 A 4/1975 King et al.
4,340,091 A 7/1982 Skelton et al.
(Continued)

FOREIGN PATENT DOCUMENTS

CN 1142351 A 2/1997
CN 106175845 A 12/2016
(Continued)

OTHER PUBLICATIONS

Al Zaibag et al., "Percutaneous Balloon Valvotomy in Tricuspid Stenosis", British Heart Journal, vol. 57, No. 1, Jan. 1987.
(Continued)

*Primary Examiner* — Thomas McEvoy
(74) *Attorney, Agent, or Firm* — Anya Adams

(57) ABSTRACT

In one embodiment, a leaflet capture device for improving the coaptation of heart valve leaflets is provided. The leaflet capture device can include a clip having a coupling member and a leaflet engagement portion. The coupling member has a lumen extending therethrough. The leaflet engagement portion is moveable toward and away from the coupling member. The leaflet capture device can be delivered by a support catheter, an inner shaft, and an actuating connector. Extending an end of the inner shaft away from the coupling member of the clip pulls the actuating connector to move the leaflet engagement portion away from the coupling member.

20 Claims, 11 Drawing Sheets

Related U.S. Application Data

(60) Provisional application No. 62/442,724, filed on Jan. 5, 2017.

(51) Int. Cl.
    *A61B 17/00*         (2006.01)
    *A61B 17/04*         (2006.01)
    *A61B 17/128*       (2006.01)
    *A61F 2/00*          (2006.01)

(52) U.S. Cl.
    CPC ............... *A61F 2210/0014* (2013.01); *A61F 2220/0016* (2013.01); *A61F 2220/0025* (2013.01); *A61F 2220/0058* (2013.01)

(56) References Cited

U.S. PATENT DOCUMENTS

| | | |
|---|---|---|
| 4,506,669 A | 3/1985 | Blake, III |
| 4,590,937 A | 5/1986 | Deniega |
| 4,693,248 A | 9/1987 | Failla |
| 4,803,983 A | 2/1989 | Siegel |
| 5,125,895 A | 6/1992 | Buchbinder et al. |
| 5,171,252 A | 12/1992 | Friedland |
| 5,195,962 A | 3/1993 | Martin et al. |
| 5,292,326 A | 3/1994 | Green et al. |
| 5,327,905 A | 7/1994 | Avitall |
| 5,363,861 A | 11/1994 | Edwards et al. |
| 5,370,685 A | 12/1994 | Stevens |
| 5,389,077 A | 2/1995 | Melinyshyn et al. |
| 5,411,552 A | 5/1995 | Andersen et al. |
| 5,450,860 A | 9/1995 | O'Connor |
| 5,456,674 A | 10/1995 | Bos et al. |
| 5,474,057 A | 12/1995 | Makower et al. |
| 5,478,353 A | 12/1995 | Yoon |
| 5,487,746 A | 1/1996 | Yu et al. |
| 5,565,004 A | 10/1996 | Christoudias |
| 5,607,462 A | 3/1997 | Imran |
| 5,609,598 A | 3/1997 | Laufer et al. |
| 5,611,794 A | 3/1997 | Sauer et al. |
| 5,626,607 A | 5/1997 | Malecki et al. |
| 5,695,504 A | 12/1997 | Gifford, III et al. |
| 5,716,417 A | 2/1998 | Girard et al. |
| 5,727,569 A | 3/1998 | Benetti et al. |
| 5,741,297 A | 4/1998 | Simon |
| 5,782,746 A | 7/1998 | Wright |
| 5,797,960 A | 8/1998 | Stevens et al. |
| 5,836,311 A | 11/1998 | Borst et al. |
| 5,843,076 A | 12/1998 | Webster, Jr. et al. |
| 5,855,590 A | 1/1999 | Malecki et al. |
| 5,885,271 A | 3/1999 | Hamilton et al. |
| 5,888,247 A | 3/1999 | Benetti |
| 5,891,017 A | 4/1999 | Swindle et al. |
| 5,891,112 A | 4/1999 | Samson |
| 5,894,843 A | 4/1999 | Benetti et al. |
| 5,921,979 A | 7/1999 | Kovac et al. |
| 5,944,738 A | 8/1999 | Amplatz et al. |
| 5,957,835 A | 9/1999 | Anderson et al. |
| 5,972,020 A | 10/1999 | Carpentier et al. |
| 5,980,534 A | 11/1999 | Gimpelson |
| 6,004,329 A | 12/1999 | Myers et al. |
| 6,010,531 A | 1/2000 | Donlon et al. |
| 6,017,358 A | 1/2000 | Yoon et al. |
| 6,086,600 A | 7/2000 | Kortenbach |
| 6,120,496 A | 9/2000 | Whayne et al. |
| 6,132,370 A | 10/2000 | Furnish et al. |
| 6,162,239 A | 12/2000 | Manhes |
| 6,165,183 A | 12/2000 | Kuehn et al. |
| 6,182,664 B1 | 2/2001 | Cosgrove |
| 6,193,732 B1 | 2/2001 | Frantzen et al. |
| 6,193,734 B1 | 2/2001 | Bolduc et al. |
| 6,200,315 B1 | 3/2001 | Gaiser et al. |
| 6,228,032 B1 | 5/2001 | Eaton et al. |
| 6,241,743 B1 | 6/2001 | Levin et al. |
| 6,269,819 B1 | 8/2001 | Oz et al. |
| 6,269,829 B1 | 8/2001 | Chen et al. |
| 6,312,447 B1 | 11/2001 | Grimes |
| 6,461,366 B1 | 10/2002 | Seguin |
| 6,468,285 B1 | 10/2002 | Hsu et al. |
| 6,508,806 B1 | 1/2003 | Hoste |
| 6,508,825 B1 | 1/2003 | Selmon et al. |
| 6,530,933 B1 | 3/2003 | Yeung et al. |
| 6,537,290 B2 | 3/2003 | Adams et al. |
| 6,544,215 B1 | 4/2003 | Bencini et al. |
| 6,626,930 B1 | 9/2003 | Allen et al. |
| 6,629,534 B1 | 10/2003 | St. Goar et al. |
| 6,719,767 B1 | 4/2004 | Kimblad |
| 6,764,510 B2 | 7/2004 | Vidlund et al. |
| 6,770,083 B2 | 8/2004 | Seguin |
| 6,837,867 B2 | 1/2005 | Kortelling |
| 6,855,137 B2 | 2/2005 | Bon |
| 6,913,614 B2 | 7/2005 | Marino et al. |
| 6,939,337 B2 | 9/2005 | Parker et al. |
| 6,945,956 B2 | 9/2005 | Waldhauser et al. |
| 7,048,754 B2 | 5/2006 | Martin et al. |
| 7,101,395 B2 | 9/2006 | Tremulis et al. |
| 7,125,421 B2 | 10/2006 | Tremulis et al. |
| 7,288,097 B2 | 10/2007 | Seguin |
| 7,371,210 B2 | 5/2008 | Brock et al. |
| 7,464,712 B2 | 12/2008 | Oz et al. |
| 7,509,959 B2 | 3/2009 | Oz et al. |
| 7,559,936 B2 | 7/2009 | Levine |
| 7,569,062 B1 | 8/2009 | Kuehn et al. |
| 7,618,449 B2 | 11/2009 | Tremulis et al. |
| 7,628,797 B2 | 12/2009 | Tieu et al. |
| 7,682,369 B2 | 3/2010 | Seguin |
| 7,731,706 B2 | 6/2010 | Potter |
| 7,744,609 B2 | 6/2010 | Allen et al. |
| 7,748,389 B2 | 7/2010 | Salahieh et al. |
| 7,753,932 B2 | 7/2010 | Gingrich et al. |
| 7,758,596 B2 | 7/2010 | Oz et al. |
| 7,780,723 B2 | 8/2010 | Taylor |
| 7,803,185 B2 | 9/2010 | Gabbay |
| 7,824,443 B2 | 11/2010 | Salahieh et al. |
| 7,981,123 B2 | 7/2011 | Seguin |
| 7,988,724 B2 | 8/2011 | Salahieh et al. |
| 8,052,750 B2 | 11/2011 | Tuval et al. |
| 8,070,805 B2 | 12/2011 | Vidlund et al. |
| 8,096,985 B2 | 1/2012 | Legaspi et al. |
| 8,104,149 B1 | 1/2012 | McGarity |
| 8,133,239 B2 | 3/2012 | Oz et al. |
| 8,147,542 B2 | 4/2012 | Maisano et al. |
| 8,172,856 B2 | 5/2012 | Eigler et al. |
| 8,206,437 B2 | 6/2012 | Bonhoeffer et al. |
| 8,216,301 B2 | 7/2012 | Bonhoeffer et al. |
| 8,303,653 B2 | 11/2012 | Bonhoeffer et al. |
| 8,313,525 B2 | 11/2012 | Tuval et al. |
| 8,348,995 B2 | 1/2013 | Tuval et al. |
| 8,348,996 B2 | 1/2013 | Tuval et al. |
| 8,414,643 B2 | 4/2013 | Tuval et al. |
| 8,425,404 B2 | 4/2013 | Wilson et al. |
| 8,449,599 B2 | 5/2013 | Chau et al. |
| 8,449,606 B2 | 5/2013 | Ellasen et al. |
| 8,460,368 B2 | 6/2013 | Taylor et al. |
| 8,470,028 B2 | 6/2013 | Thornton et al. |
| 8,480,730 B2 | 7/2013 | Maurer et al. |
| 8,496,671 B1 | 7/2013 | Hausen |
| 8,540,767 B2 | 9/2013 | Zhang |
| 8,579,965 B2 | 11/2013 | Bonhoeffer et al. |
| 8,585,756 B2 | 11/2013 | Bonhoeffer et al. |
| 8,652,202 B2 | 2/2014 | Alon et al. |
| 8,668,733 B2 | 3/2014 | Haug et al. |
| 8,721,665 B2 | 5/2014 | Oz et al. |
| 8,734,505 B2 | 5/2014 | Goldfarb et al. |
| 8,740,918 B2 | 6/2014 | Seguin |
| 8,771,347 B2 | 7/2014 | DeBoer et al. |
| 8,778,017 B2 | 7/2014 | Ellasen et al. |
| 8,834,564 B2 | 9/2014 | Tuval et al. |
| 8,840,663 B2 | 9/2014 | Salahieh et al. |
| 8,876,894 B2 | 11/2014 | Tuval et al. |
| 8,876,895 B2 | 11/2014 | Tuval et al. |
| 8,945,177 B2 | 2/2015 | Dell et al. |
| 9,034,032 B2 | 5/2015 | McLean et al. |
| 9,044,246 B2 | 6/2015 | Goldfarb et al. |

(56) References Cited

U.S. PATENT DOCUMENTS

| | | |
|---|---|---|
| 9,198,757 B2 | 12/2015 | Schroeder et al. |
| 9,220,507 B1 | 12/2015 | Patel et al. |
| 9,259,317 B2 | 2/2016 | Wilson et al. |
| 9,282,972 B1 | 3/2016 | Patel et al. |
| 9,301,834 B2 | 4/2016 | Tuval et al. |
| 9,308,360 B2 | 4/2016 | Bishop et al. |
| 9,387,071 B2 | 7/2016 | Tuval et al. |
| 9,427,327 B2 | 8/2016 | Parrish |
| 9,439,763 B2 | 9/2016 | Geist et al. |
| 9,510,837 B2 | 12/2016 | Seguin |
| 9,510,946 B2 | 12/2016 | Chau et al. |
| 9,572,660 B2 | 2/2017 | Braido et al. |
| 9,642,704 B2 | 5/2017 | Tuval et al. |
| 9,700,445 B2 | 7/2017 | Martin et al. |
| 9,775,963 B2 | 10/2017 | Miller |
| D809,139 S | 1/2018 | Marsot et al. |
| 9,889,002 B2 | 2/2018 | Bonhoeffer et al. |
| 9,949,824 B2 | 4/2018 | Bonhoeffer et al. |
| 10,076,327 B2 | 9/2018 | Ellis et al. |
| 10,076,415 B1 | 9/2018 | Metchik et al. |
| 10,099,050 B2 | 10/2018 | Chen et al. |
| 10,105,221 B2 | 10/2018 | Siegel |
| 10,105,222 B1 | 10/2018 | Metchik et al. |
| 10,111,751 B1 | 10/2018 | Metchik et al. |
| 10,123,873 B1 | 11/2018 | Metchik et al. |
| 10,130,475 B1 | 11/2018 | Metchik et al. |
| 10,136,993 B1 | 11/2018 | Metchik et al. |
| 10,159,570 B1 | 12/2018 | Metchik et al. |
| 10,226,309 B2 | 3/2019 | Ho et al. |
| 10,231,837 B1 | 3/2019 | Metchik et al. |
| 10,238,493 B1 | 3/2019 | Metchik et al. |
| 10,238,494 B2 | 3/2019 | McNiven et al. |
| 10,238,495 B2 | 3/2019 | Marsot et al. |
| 10,299,924 B2 | 5/2019 | Kizuka |
| 10,376,673 B2 | 8/2019 | Van Hoven et al. |
| 10,575,841 B1 | 3/2020 | Paulos |
| 2001/0005787 A1 | 6/2001 | Oz et al. |
| 2002/0013571 A1 | 1/2002 | Goldfarb et al. |
| 2002/0107531 A1 | 8/2002 | Schreck et al. |
| 2002/0173811 A1 | 11/2002 | Tu et al. |
| 2002/0183787 A1 | 12/2002 | Wahr et al. |
| 2003/0144573 A1 | 7/2003 | Heilman et al. |
| 2003/0187467 A1 | 10/2003 | Schreck |
| 2003/0208231 A1 | 11/2003 | Williamson et al. |
| 2004/0003819 A1 | 1/2004 | St. Goar et al. |
| 2004/0030382 A1 | 2/2004 | St. Goar et al. |
| 2004/0034365 A1 | 2/2004 | Lentz et al. |
| 2004/0044350 A1 | 3/2004 | Martin et al. |
| 2004/0044365 A1 | 3/2004 | Bachman |
| 2004/0049207 A1 | 3/2004 | Goldfarb et al. |
| 2004/0122448 A1 | 6/2004 | Levine |
| 2004/0127981 A1 | 7/2004 | Rahdert et al. |
| 2004/0127982 A1 | 7/2004 | Machold et al. |
| 2004/0147943 A1 | 7/2004 | Kobayashi |
| 2004/0181135 A1 | 9/2004 | Drysen |
| 2004/0181206 A1 | 9/2004 | Chiu et al. |
| 2004/0181238 A1 | 9/2004 | Zarbatany et al. |
| 2004/0210307 A1 | 10/2004 | Khairkhahan |
| 2004/0220593 A1 | 11/2004 | Greenhalgh |
| 2005/0010287 A1 | 1/2005 | Macoviak et al. |
| 2005/0049618 A1 | 3/2005 | Masuda et al. |
| 2005/0070926 A1 | 3/2005 | Ortiz |
| 2005/0137690 A1 | 6/2005 | Salahieh et al. |
| 2005/0143767 A1 | 6/2005 | Kimura et al. |
| 2005/0165429 A1 | 7/2005 | Douglas et al. |
| 2005/0216039 A1 | 9/2005 | Lederman |
| 2005/0251183 A1 | 11/2005 | Buckman et al. |
| 2005/0288786 A1 | 12/2005 | Chanduszko |
| 2006/0020275 A1 | 1/2006 | Goldfarb et al. |
| 2006/0089671 A1 | 4/2006 | Goldfarb et al. |
| 2006/0100649 A1 | 5/2006 | Hart |
| 2006/0122647 A1 | 6/2006 | Callaghan et al. |
| 2006/0142694 A1 | 6/2006 | Bednarek et al. |
| 2006/0173251 A1 | 8/2006 | Govari et al. |
| 2006/0178700 A1 | 8/2006 | Quinn |
| 2006/0224169 A1 | 10/2006 | Weisenburgh et al. |
| 2007/0010800 A1 | 1/2007 | Weitzner et al. |
| 2007/0010877 A1 | 1/2007 | Salahieh et al. |
| 2007/0016286 A1 | 1/2007 | Herrmann et al. |
| 2007/0021779 A1 | 1/2007 | Garvin et al. |
| 2007/0032807 A1 | 2/2007 | Ortiz et al. |
| 2007/0093857 A1 | 4/2007 | Rogers et al. |
| 2007/0093890 A1 | 4/2007 | Eliasen et al. |
| 2007/0100356 A1* | 5/2007 | Lucatero ............... A61B 17/08 606/139 |
| 2007/0156197 A1 | 7/2007 | Root et al. |
| 2007/0191154 A1 | 8/2007 | Genereux et al. |
| 2007/0197858 A1 | 8/2007 | Goldfarb et al. |
| 2007/0198038 A1 | 8/2007 | Cohen et al. |
| 2007/0265700 A1 | 11/2007 | Eliasen et al. |
| 2007/0282414 A1 | 12/2007 | Soltis et al. |
| 2007/0293943 A1 | 12/2007 | Quinn |
| 2007/0299387 A1 | 12/2007 | Williams et al. |
| 2007/0299424 A1 | 12/2007 | Cumming et al. |
| 2008/0039743 A1 | 2/2008 | Fox et al. |
| 2008/0039953 A1 | 2/2008 | Davis et al. |
| 2008/0051807 A1 | 2/2008 | St. Goar et al. |
| 2008/0065149 A1 | 3/2008 | Thielen et al. |
| 2008/0077144 A1 | 3/2008 | Crofford |
| 2008/0091169 A1 | 4/2008 | Heideman et al. |
| 2008/0140089 A1 | 6/2008 | Kogiso et al. |
| 2008/0147093 A1 | 6/2008 | Roskopf et al. |
| 2008/0147112 A1 | 6/2008 | Sheets et al. |
| 2008/0149685 A1 | 6/2008 | Smith et al. |
| 2008/0167713 A1 | 7/2008 | Bolling |
| 2008/0177300 A1 | 7/2008 | Mas et al. |
| 2008/0208332 A1 | 8/2008 | Lamphere et al. |
| 2008/0221672 A1 | 9/2008 | Lamphere et al. |
| 2008/0255427 A1 | 10/2008 | Satake et al. |
| 2008/0281356 A1 | 11/2008 | Chau et al. |
| 2008/0281411 A1 | 11/2008 | Berreklouw |
| 2008/0287862 A1 | 11/2008 | Weitzner et al. |
| 2008/0294247 A1 | 11/2008 | Yang et al. |
| 2008/0312506 A1 | 12/2008 | Spivey et al. |
| 2008/0319455 A1 | 12/2008 | Harris et al. |
| 2009/0005863 A1 | 1/2009 | Goetz et al. |
| 2009/0024110 A1 | 1/2009 | Heideman et al. |
| 2009/0131880 A1 | 5/2009 | Speziali et al. |
| 2009/0156995 A1 | 6/2009 | Martin et al. |
| 2009/0163934 A1 | 6/2009 | Raschdorf, Jr. et al. |
| 2009/0166913 A1 | 7/2009 | Guo et al. |
| 2009/0177266 A1 | 7/2009 | Powell et al. |
| 2009/0234280 A1 | 9/2009 | Tah et al. |
| 2009/0275902 A1 | 11/2009 | Heeps et al. |
| 2009/0287304 A1 | 11/2009 | Dahlgren et al. |
| 2010/0022823 A1 | 1/2010 | Goldfarb et al. |
| 2010/0057192 A1 | 3/2010 | Celermajer |
| 2010/0069834 A1 | 3/2010 | Schultz |
| 2010/0094317 A1 | 4/2010 | Goldfarb et al. |
| 2010/0106141 A1 | 4/2010 | Osypka et al. |
| 2010/0121434 A1 | 5/2010 | Paul et al. |
| 2010/0249497 A1 | 9/2010 | Peine et al. |
| 2010/0298929 A1 | 11/2010 | Thornton et al. |
| 2010/0324595 A1 | 12/2010 | Linder et al. |
| 2011/0082538 A1 | 4/2011 | Dahlgren et al. |
| 2011/0137410 A1 | 6/2011 | Hacohen |
| 2011/0245855 A1 | 10/2011 | Matsuoka et al. |
| 2011/0257723 A1 | 10/2011 | McNamara |
| 2011/0295281 A1 | 12/2011 | Mizumoto et al. |
| 2012/0022633 A1 | 1/2012 | Olson et al. |
| 2012/0041453 A1 | 2/2012 | Klingenbeck |
| 2012/0089125 A1 | 4/2012 | Scheibe et al. |
| 2012/0109160 A1 | 5/2012 | Martinez et al. |
| 2012/0116419 A1 | 5/2012 | Sigmon, Jr. |
| 2012/0209318 A1 | 8/2012 | Qadeer |
| 2012/0277853 A1 | 11/2012 | Rothstein |
| 2013/0035759 A1 | 2/2013 | Gross et al. |
| 2013/0041314 A1 | 2/2013 | Dillon |
| 2013/0066341 A1 | 3/2013 | Ketai et al. |
| 2013/0066342 A1 | 3/2013 | Dell et al. |
| 2013/0072945 A1 | 3/2013 | Terada |
| 2013/0073034 A1 | 3/2013 | Wilson et al. |
| 2013/0110254 A1 | 5/2013 | Osborne |
| 2013/0190798 A1 | 7/2013 | Kapadia |

(56) References Cited

U.S. PATENT DOCUMENTS

| | | |
|---|---|---|
| 2013/0190861 A1 | 7/2013 | Chau et al. |
| 2013/0268069 A1 | 10/2013 | Zakai et al. |
| 2013/0282059 A1 | 10/2013 | Ketai et al. |
| 2013/0304197 A1 | 11/2013 | Buchbinder et al. |
| 2013/0325110 A1 | 12/2013 | Khalil et al. |
| 2014/0031864 A1 | 1/2014 | Jafari et al. |
| 2014/0031928 A1 | 1/2014 | Murphy et al. |
| 2014/0046433 A1 | 2/2014 | Kovalsky |
| 2014/0046434 A1 | 2/2014 | Rolando et al. |
| 2014/0052237 A1 | 2/2014 | Lane et al. |
| 2014/0058411 A1 | 2/2014 | Soutorine et al. |
| 2014/0067048 A1 | 3/2014 | Chau et al. |
| 2014/0067052 A1 | 3/2014 | Chau et al. |
| 2014/0094903 A1 | 4/2014 | Miller et al. |
| 2014/0135685 A1 | 5/2014 | Kabe et al. |
| 2014/0194975 A1 | 7/2014 | Quill et al. |
| 2014/0200662 A1 | 7/2014 | Eftel et al. |
| 2014/0207231 A1 | 7/2014 | Hacohen et al. |
| 2014/0236198 A1 | 8/2014 | Goldfarb et al. |
| 2014/0243860 A1 | 8/2014 | Morris et al. |
| 2014/0243968 A1 | 8/2014 | Padala |
| 2014/0251042 A1 | 9/2014 | Asselin et al. |
| 2014/0276971 A1 | 9/2014 | Kovach |
| 2014/0277404 A1 | 9/2014 | Wilson et al. |
| 2014/0277411 A1 | 9/2014 | Bortlein et al. |
| 2014/0277427 A1 | 9/2014 | Ratz et al. |
| 2014/0316428 A1 | 10/2014 | Golan |
| 2014/0324164 A1 | 10/2014 | Gross et al. |
| 2014/0330368 A1 | 11/2014 | Gloss et al. |
| 2014/0336751 A1 | 11/2014 | Kramer |
| 2014/0371843 A1 | 12/2014 | Wilson et al. |
| 2015/0039084 A1 | 2/2015 | Levi et al. |
| 2015/0057704 A1 | 2/2015 | Takahashi |
| 2015/0094802 A1 | 4/2015 | Buchbinder et al. |
| 2015/0100116 A1 | 4/2015 | Mohl et al. |
| 2015/0105808 A1 | 4/2015 | Gordon et al. |
| 2015/0148896 A1 | 5/2015 | Karapetian et al. |
| 2015/0157268 A1 | 6/2015 | Winshtein et al. |
| 2015/0196390 A1 | 7/2015 | Ma et al. |
| 2015/0223793 A1 | 8/2015 | Goldfarb et al. |
| 2015/0230919 A1 | 8/2015 | Chau et al. |
| 2015/0238313 A1 | 8/2015 | Spence et al. |
| 2015/0257757 A1 | 9/2015 | Powers et al. |
| 2015/0257877 A1 | 9/2015 | Hernandez |
| 2015/0257883 A1 | 9/2015 | Basude et al. |
| 2015/0313592 A1 | 11/2015 | Coillard-Lavirotte et al. |
| 2015/0351904 A1 | 12/2015 | Cooper et al. |
| 2015/0366666 A1 | 12/2015 | Khairkhahan et al. |
| 2016/0008131 A1 | 1/2016 | Christianson et al. |
| 2016/0022406 A1 | 1/2016 | Zhang |
| 2016/0022970 A1 | 1/2016 | Forcucci et al. |
| 2016/0051796 A1 | 2/2016 | Kanemasa et al. |
| 2016/0074164 A1 | 3/2016 | Naor |
| 2016/0074165 A1 | 3/2016 | Spence et al. |
| 2016/0106539 A1 | 4/2016 | Buchbinder et al. |
| 2016/0113762 A1 | 4/2016 | Clague et al. |
| 2016/0113764 A1 | 4/2016 | Sheahan et al. |
| 2016/0113766 A1 | 4/2016 | Ganesan et al. |
| 2016/0155987 A1 | 6/2016 | Yoo et al. |
| 2016/0174979 A1 | 6/2016 | Wei |
| 2016/0174981 A1 | 6/2016 | Fago et al. |
| 2016/0242906 A1 | 8/2016 | Morriss et al. |
| 2016/0287387 A1 | 10/2016 | Wei |
| 2016/0302811 A1 | 10/2016 | Rodriguez-Navarro et al. |
| 2016/0317290 A1 | 11/2016 | Chau et al. |
| 2016/0331523 A1 | 11/2016 | Chau et al. |
| 2016/0354082 A1 | 12/2016 | Oz et al. |
| 2017/0020521 A1 | 1/2017 | Krone et al. |
| 2017/0035561 A1 | 2/2017 | Rowe et al. |
| 2017/0035566 A1 | 2/2017 | Krone et al. |
| 2017/0042456 A1 | 2/2017 | Budiman |
| 2017/0042678 A1 | 2/2017 | Ganesan et al. |
| 2017/0049455 A1 | 2/2017 | Seguin |
| 2017/0100119 A1 | 4/2017 | Baird et al. |
| 2017/0100236 A1 | 4/2017 | Robertson et al. |
| 2017/0224955 A1 | 8/2017 | Douglas et al. |
| 2017/0239048 A1 | 8/2017 | Goldfarb et al. |
| 2017/0252154 A1 | 9/2017 | Tubishevitz et al. |
| 2017/0266413 A1 | 9/2017 | Khuu et al. |
| 2017/0281330 A1 | 10/2017 | Liljegren et al. |
| 2017/0348102 A1 | 12/2017 | Cousins et al. |
| 2018/0008311 A1 | 1/2018 | Shiroff et al. |
| 2018/0021044 A1 | 1/2018 | Miller et al. |
| 2018/0021129 A1 | 1/2018 | Peterson et al. |
| 2018/0021134 A1 | 1/2018 | McNiven et al. |
| 2018/0078271 A1 | 3/2018 | Thrasher, III |
| 2018/0078361 A1 | 3/2018 | Naor et al. |
| 2018/0092661 A1 | 4/2018 | Prabhu |
| 2018/0126124 A1 | 5/2018 | Winston et al. |
| 2018/0133008 A1 | 5/2018 | Kizuka et al. |
| 2018/0146964 A1 | 5/2018 | Garcia et al. |
| 2018/0146966 A1 | 5/2018 | Hernandez et al. |
| 2018/0153552 A1 | 6/2018 | King et al. |
| 2018/0161159 A1 | 6/2018 | Lee et al. |
| 2018/0168803 A1 | 6/2018 | Pesce et al. |
| 2018/0185154 A1 | 7/2018 | Cao |
| 2018/0221147 A1 | 8/2018 | Ganesan et al. |
| 2018/0235657 A1 | 8/2018 | Abunassar |
| 2018/0243086 A1 | 8/2018 | Barbarino et al. |
| 2018/0258665 A1 | 9/2018 | Reddy et al. |
| 2018/0263767 A1 | 9/2018 | Chau et al. |
| 2018/0296326 A1 | 10/2018 | Dixon et al. |
| 2018/0296327 A1 | 10/2018 | Dixon et al. |
| 2018/0296328 A1 | 10/2018 | Dixon et al. |
| 2018/0296329 A1 | 10/2018 | Dixon et al. |
| 2018/0296330 A1 | 10/2018 | Dixon et al. |
| 2018/0296331 A1 | 10/2018 | Dixon et al. |
| 2018/0296332 A1 | 10/2018 | Dixon et al. |
| 2018/0296333 A1 | 10/2018 | Dixon et al. |
| 2018/0296334 A1 | 10/2018 | Dixon et al. |
| 2018/0325661 A1 | 11/2018 | Delgado et al. |
| 2018/0325671 A1 | 11/2018 | Abunassar et al. |
| 2018/0333259 A1 | 11/2018 | Dibie |
| 2018/0344457 A1 | 12/2018 | Gross et al. |
| 2018/0353181 A1 | 12/2018 | Wei |
| 2019/0000613 A1 | 1/2019 | Delgado et al. |
| 2019/0000623 A1 | 1/2019 | Pan et al. |
| 2019/0008642 A1 | 1/2019 | Delgado et al. |
| 2019/0008643 A1 | 1/2019 | Delgado et al. |
| 2019/0015199 A1 | 1/2019 | Delgado et al. |
| 2019/0015200 A1 | 1/2019 | Delgado et al. |
| 2019/0015207 A1 | 1/2019 | Delgado et al. |
| 2019/0015208 A1 | 1/2019 | Delgado et al. |
| 2019/0021851 A1 | 1/2019 | Delgado et al. |
| 2019/0021852 A1 | 1/2019 | Delgado et al. |
| 2019/0029498 A1 | 1/2019 | Mankowski et al. |
| 2019/0029810 A1 | 1/2019 | Delgado et al. |
| 2019/0029813 A1 | 1/2019 | Delgado et al. |
| 2019/0030285 A1 | 1/2019 | Prabhu et al. |
| 2019/0053810 A1 | 2/2019 | Griffin |
| 2019/0060058 A1 | 2/2019 | Delgado et al. |
| 2019/0060059 A1 | 2/2019 | Delgado et al. |
| 2019/0060072 A1 | 2/2019 | Zeng |
| 2019/0060073 A1 | 2/2019 | Delgado et al. |
| 2019/0060074 A1 | 2/2019 | Delgado et al. |
| 2019/0060075 A1 | 2/2019 | Delgado et al. |
| 2019/0069991 A1 | 3/2019 | Metchik et al. |
| 2019/0069992 A1 | 3/2019 | Delgado et al. |
| 2019/0069993 A1 | 3/2019 | Delgado et al. |
| 2019/0105156 A1 | 4/2019 | He et al. |
| 2019/0111239 A1 | 4/2019 | Bolduc et al. |
| 2019/0117113 A1 | 4/2019 | Curran |
| 2019/0142589 A1 | 5/2019 | Basude |
| 2019/0159782 A1 | 5/2019 | Kamaraj et al. |
| 2019/0167197 A1 | 6/2019 | Abunassar et al. |
| 2019/0183644 A1 | 6/2019 | Hacohen |
| 2019/0192296 A1 | 6/2019 | Schwartz et al. |
| 2019/0209323 A1 | 7/2019 | Metchik et al. |
| 2019/0261995 A1 | 8/2019 | Goldfarb et al. |
| 2019/0261996 A1 | 8/2019 | Goldfarb et al. |
| 2019/0261997 A1 | 8/2019 | Goldfarb et al. |
| 2019/0314155 A1 | 10/2019 | Franklin et al. |
| 2019/0321166 A1 | 10/2019 | Freschauf et al. |
| 2020/0113683 A1 | 4/2020 | Dale et al. |

(56) References Cited

U.S. PATENT DOCUMENTS

| | | |
|---|---|---|
| 2020/0138569 A1 | 5/2020 | Basude et al. |
| 2020/0205979 A1 | 7/2020 | O'Carroll et al. |
| 2020/0237512 A1 | 7/2020 | McCann et al. |
| 2020/0337842 A1 | 10/2020 | Metchik et al. |
| 2020/0360054 A1 | 11/2020 | Walsh et al. |
| 2020/0360132 A1 | 11/2020 | Spence |
| 2020/0368016 A1 | 11/2020 | Pesce et al. |
| 2021/0022850 A1 | 1/2021 | Basude et al. |
| 2021/0059680 A1 | 3/2021 | Lin et al. |
| 2021/0169650 A1 | 6/2021 | Dai et al. |
| 2021/0186698 A1 | 6/2021 | Abunassar et al. |
| 2021/0251757 A1 | 8/2021 | Siegel et al. |
| 2021/0259835 A1 | 8/2021 | Tyler, II et al. |
| 2021/0267781 A1 | 9/2021 | Metchik et al. |
| 2021/0307900 A1 | 10/2021 | Hacohen |
| 2021/0330456 A1 | 10/2021 | Hacohen et al. |
| 2021/0338418 A1 | 11/2021 | Feld |
| 2021/0361416 A1 | 11/2021 | Stearns |
| 2021/0361422 A1 | 11/2021 | Gross et al. |
| 2021/0361428 A1 | 11/2021 | Dixon |
| 2021/0378818 A1 | 12/2021 | Manash et al. |
| 2021/0401434 A1 | 12/2021 | Tien et al. |
| 2022/0039943 A1 | 2/2022 | Phan |
| 2022/0039954 A1 | 2/2022 | Nia et al. |
| 2022/0071767 A1 | 3/2022 | Dixon et al. |
| 2022/0133327 A1 | 5/2022 | Zhang et al. |
| 2022/0142780 A1 | 5/2022 | Zhang et al. |
| 2022/0142781 A1 | 5/2022 | Zhang et al. |
| 2022/0226108 A1 | 7/2022 | Freschauf et al. |
| 2022/0233312 A1 | 7/2022 | Delgado et al. |
| 2022/0257196 A1 | 8/2022 | Massmann |
| 2022/0287841 A1 | 9/2022 | Freschauf et al. |
| 2022/0313433 A1 | 10/2022 | Ma et al. |
| 2023/0014540 A1 | 1/2023 | Metchik et al. |
| 2023/0149170 A1 | 5/2023 | Giese et al. |
| 2023/0218291 A1 | 7/2023 | Zarbatany et al. |
| 2023/0270549 A1 | 8/2023 | Guidotti et al. |

FOREIGN PATENT DOCUMENTS

| | | |
|---|---|---|
| CN | 106491245 A | 3/2017 |
| CN | 107789017 A | 3/2018 |
| CN | 109953779 A | 7/2019 |
| CN | 110338857 A | 10/2019 |
| CN | 110495972 A | 11/2019 |
| CN | 110537946 A | 12/2019 |
| CN | 110664515 A | 1/2020 |
| CN | 209996540 U | 1/2020 |
| CN | 211723546 U | 10/2020 |
| CN | 111870398 A | 11/2020 |
| CN | 111904660 A | 11/2020 |
| CN | 112120831 A | 12/2020 |
| CN | 112168427 A | 1/2021 |
| CN | 112190367 A | 1/2021 |
| CN | 212346813 U | 1/2021 |
| CN | 212415988 U | 1/2021 |
| CN | 212490263 U | 2/2021 |
| CN | 113476182 A | 10/2021 |
| CN | 113855328 A | 12/2021 |
| CN | 215019733 U | 12/2021 |
| EP | 0098100 A2 | 1/1984 |
| EP | 1674040 A2 | 6/2006 |
| FR | 2146050 A5 | 2/1973 |
| FR | 9711600 | 3/1997 |
| IN | 211243911 U | 8/2020 |
| WO | 2014064694 A2 | 5/2014 |
| WO | 2017015632 A1 | 1/2017 |
| WO | 2018013856 A1 | 1/2018 |
| WO | 2018050200 A1 | 3/2018 |
| WO | 2018050203 A1 | 3/2018 |
| WO | 2018195015 A1 | 10/2018 |
| WO | 2018195201 A1 | 10/2018 |
| WO | 2018195215 A2 | 10/2018 |
| WO | 2019139904 A1 | 7/2019 |
| WO | 2020106705 A1 | 5/2020 |
| WO | 2020106827 A1 | 5/2020 |
| WO | 2020112622 A1 | 6/2020 |
| WO | 2020167677 A1 | 8/2020 |
| WO | 2020168081 A1 | 8/2020 |
| WO | 2020172224 A1 | 8/2020 |
| WO | 2020176410 A1 | 9/2020 |
| WO | 2021196580 A1 | 10/2021 |
| WO | 2021227412 A1 | 11/2021 |
| WO | 2022006087 A2 | 1/2022 |
| WO | 2022036209 A1 | 2/2022 |
| WO | 2022051241 A1 | 3/2022 |
| WO | 2022052506 A1 | 3/2022 |
| WO | 2022068188 A1 | 4/2022 |
| WO | 2022101817 A2 | 5/2022 |
| WO | 2022140175 A1 | 6/2022 |
| WO | 2022153131 A1 | 7/2022 |
| WO | 2022155298 A2 | 7/2022 |
| WO | 2022157592 A1 | 7/2022 |
| WO | 2022212172 A1 | 10/2022 |
| WO | 2023003755 A1 | 1/2023 |
| WO | 2023004098 A1 | 1/2023 |
| WO | 2023278663 A2 | 1/2023 |
| WO | 2023288003 A1 | 1/2023 |

OTHER PUBLICATIONS

Al-Khaja et al., "Eleven Years' Experience with Carpentier-Edwards Biological Valves in Relation to Survival and Complications", European Journal of Cardio-thoracic Surgery 3: pp. 305-311, 1989.

Almagor et al., "Balloon Expandable Stent Implantation in Stenotic Right Heart Valved Conduits", Journal of the American College of Cardiology, vol. 16, No. 5, pp. 1310-1314, Nov. 15, 1990.

Andersen, et al., "Transluminal implantation of artificial heart valves. Description of a new expandable aortic valve and initial results with implantation by catheter technique in closed chest pigs." European Heart Journal (1992), 13, 704-708.

Andersen, H.R. "History of Percutaneous Aortic Valve Prosthesis," Herz No. 34. pp. 343-346. 2009.

Batista RJ et al., "Partial left ventriculectomy to treat end-stage heart disease", Ann Thorac Surg., vol. 64, Issue—3, pp. 634-638, Sep. 1997.

Beall AC Jr. et al.,"Clinical experience with a dacron velour-covered teflon-disc mitral-valve prosthesis", Ann Thorac Surg., vol.—5, Issue 5, pp. 402-410, May 1968.

Benchimol et al., "Simultaneous Left Ventricular Echocardiography and Aortic Blood Velocity During Rapid Right Ventricular Pacing in Man", The American Journal of the Medical Sciences, vol. 273, No. 1, pp. 55-62, 1977.

Dake et al., "Transluminal Placement of Endovascular Stent-Grafts for the Treatment of Descending Thoracic Aortic Aneurysms", The New England Journal of Medicine, vol. 331, No. 26, pp. 1729-1734, Dec. 29, 1994.

Dotter et al., "Transluminal Treatment of Arteriosclerotic Obstruction: Description of a New Technic and a Preliminary Report of Its Application", Circulation, vol. XXX, pp. 654-670, 1964.

Fucci et al., "Improved results with mitral valve repair using new surgical techniques", Eur J Cardiothorac Surg. 1995;Issue 9, vol. 11, pp. 621-626.

Inoune, M.D., Kanji, et al., "Clinical Application of Transvenous Mitral Commissurotomy by a New Balloon Catheter," The Journal of Thoracic and Cardiovascular Surgery 87:394-402, 1984.

Kolata, Gina "Device That Opens Clogged Arteries Gets a Falling Grade in a New Study", The New York Times, Jan. 3, 1991, pp. 1-2 [online], [retrieved on Jul. 29, 2009]. Retrieved from the Internet <URL:http://www.nytimes.com/1991/01/03/health/device-that-opens-clogged-arteries-gets-a-faili . . . .

Lawrence, Jr., et al., "Percutaneous Endovascular Graft: Experimental Evaluation", Cardiovascular Radiology 163, pp. 357-360, May 1987.

Maisano F et al., 'The edge-to-edge technique: a simplified method to correct mitral insufficiency', Eur J Cardiothorac Surg., vol. 13, Issue—3, pp. 240-245, Mar. 1998.

(56) References Cited

OTHER PUBLICATIONS

Pavcnik, M.D., Ph.D., Dusan, et al. "Development and Initial Experimental Evaluation of a Prosthetic Aortic Valve for Transcatheter Placement," Cardiovascular Radiology 1992; 183:151-154.
Porstmann et al., "Der Verschluß des Ductus Arteriosus Persistens Ohne Thorakotomie", Thoraxchirurgie Vaskuläre Chirurgie, Band 15, Heft 2, Stuttgart, im Apr. 1967, pp. 199-203.
Praz et al., "Compassionate use of the PASCAL transcatheter mitral valve repair system for patients with severe mitral regurgitation: a multicentre, prospective, observational, first-in-man study," Lancet vol. 390, pp. 773-780, 2017.
Rashkind et al., "Creation of an Atrial Septal Defect Without Thoracotomy: A Pallative Approach to Complete Transposition of the Great Arteries", The Journal of the American Medical Association, vol. 196, No. 11, pp. 173-174, Jun. 13, 1956.
Rashkind et al., "Historical Aspects of Interventional Cardiology: Past, Present, and Future", Texas Heart Institute Journal, Interventional Cardiology, vol. 13, No. 4, pp. 363-367, Dec. 1986.
Reul RM et al., "Mitral valve reconstruction for mitral insufficiency", Prog Cardiovasc Dis., vol. 39, Issue—6, May-Jun. 1997.
Rosch, M.D., Josef, "The Birth, Early Years and Future of Interventional Radiology," J Vasc Interv Radiol 2003; 14:841-853.
Sabbah et al., "Mechanical Factors in the Degeneration of Porcine Bioprosthetic Valves: An Overview", Journal of Cardiac Surgery, vol. 4, No. 4, pp. 302-309, Dec. 1989.
Selby et al., "Experience with New Retrieval Forceps for Foreign Body Removal in the Vascular, Urinary, and Biliary Systems", Radiology: 176. pp. 535-538, 1990.
Serruys et al., "Stenting of Coronary Arteries. Are we the Sorcerer's Apprentice?", European Heart Journal, 10, 774-782, pp. 37-45, 1989.
Sigwart, Ulrich, "An Overview of Intravascular Stents: Old and New," Chapter 48, Textbook of Interventional Cardiology, 2nd Edition, W.B. Saunders Company, Philadelphia, PA, © 1994, 1990, pp. 803-815.
Uchida et al., "Modifications of Gianturco Expandable Wire Stents", Technical Note, American Roentgen Ray Society, pp. 1185-1187, May 1988.
Umaña JP et al., Bow-tie' mitral valve repair: an adjuvant technique for ischemic mitral regurgitation', Ann Thorac Surg., vol. 66, Issue—6, pp. 1640-1646, Nov. 1998.
Urban, Philip MD, "Coronary Artery Stenting", Editions Medecine et Hygiene, Geneve, pp. 1-47, 1991.
Watt et al., "Intravenous Adenosine in the Treatment of Supraventricular Tachycardia: A Dose-Ranging Study and Interaction with Dipyridamole", Br. J. Clin. Pharmac. 21, pp. 227-230, 1986.
Wheatley, David J., "Valve Prosthesis", Rob & Smith's Operative Surgery, pp. 415-424, 1986.
Grasso et al., "The PASCAL transcatheter mitral valve repair system for the treatment of mitral regurgitation: another piece to the puzzle of edge-to-edge technique", Journal of Thoracic Disease, vol. 9, No. 12, pp. 4856-4859, Dec. 2017, doi:10.21037/jtd.2017.10.156, AME Publishing Company, Hong Kong, China.

\* cited by examiner

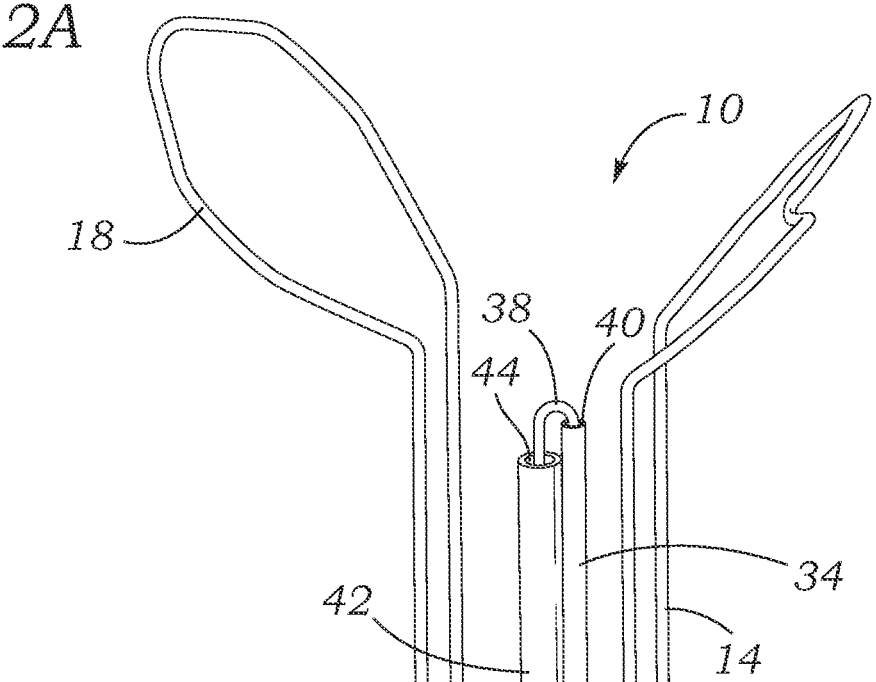
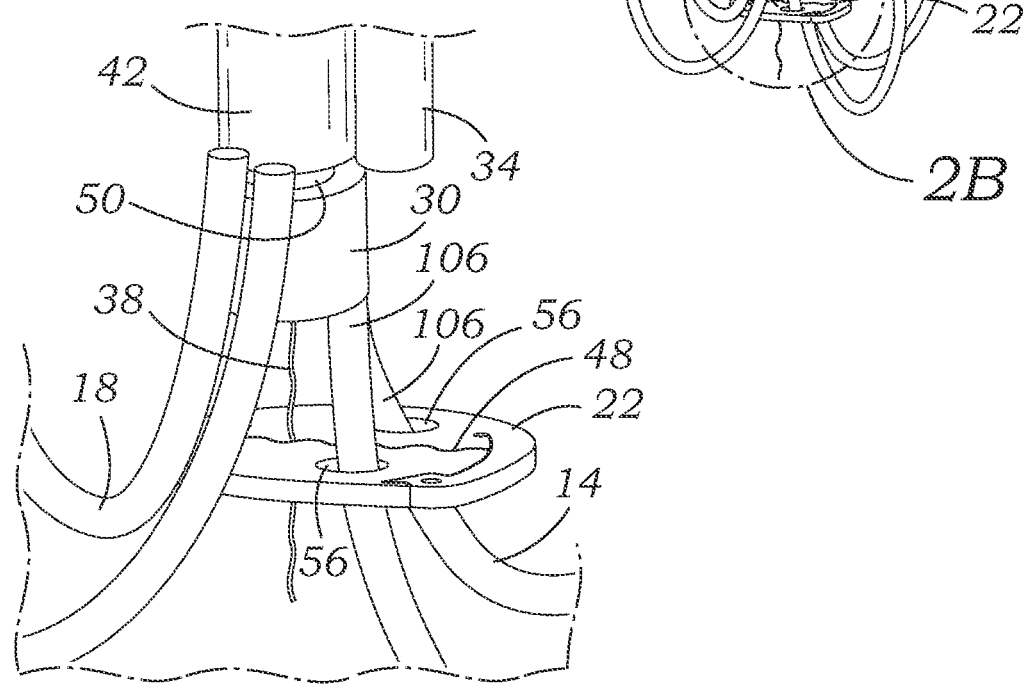

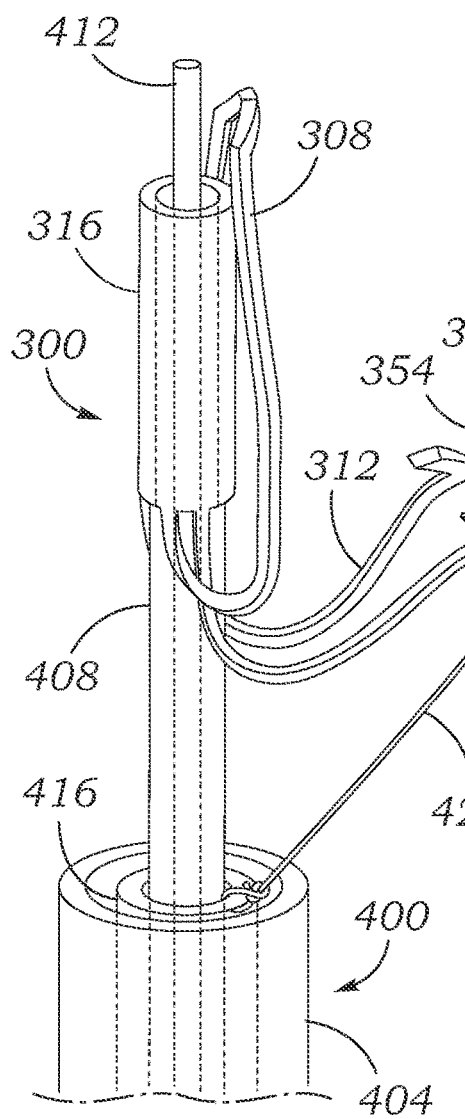
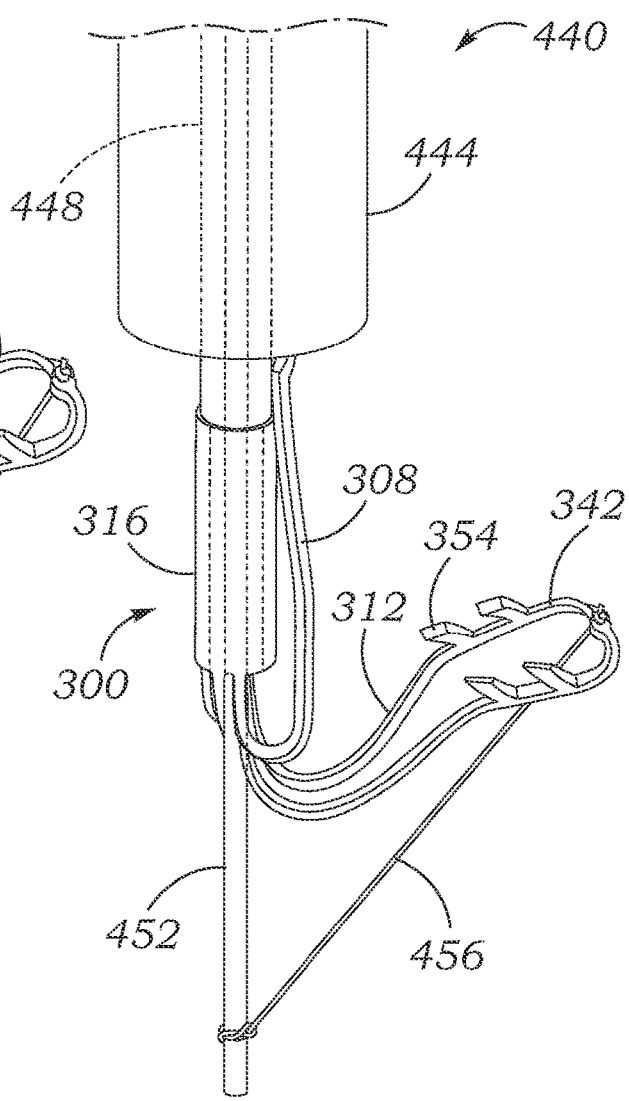
Fig. 10A
Fig. 10B

HEART VALVE COAPTATION DEVICE

CROSS REFERENCE TO RELATED APPLICATION

This application is a continuation of U.S. patent application Ser. No. 15/843,995, filed on Dec. 15, 2017, which claims the benefit of U.S. Provisional Patent Application No. 62/442,724, filed Jan. 5, 2017, which is incorporated herein by reference.

FIELD

The present disclosure generally relates to heart valve repair, and more particularly to devices and related methods for improving coaptation between heart valve leaflets.

BACKGROUND

The native heart valves (i.e., the aortic, pulmonary, tricuspid, and mitral valves) serve critical functions in assuring the unidirectional flow of an adequate supply of blood through the cardiovascular system. These heart valves can be rendered less effective by congenital malformations, inflammatory processes, infectious conditions, or disease. Such damage to the valves can result in serious cardiovascular compromise or death.

For many years the definitive treatment for such disorders was the surgical repair or replacement of the valve during open heart surgery. However, such surgeries are highly invasive, and are prone to many complications. Therefore, elderly and frail patients with defective heart valves often went untreated. More recently, transcatheter techniques have been developed for introducing and implanting prosthetic devices in a manner that is much less invasive than open heart surgery. Such transcatheter techniques have increased in popularity due to their high success rates.

A healthy heart has a generally conical shape that tapers to a lower apex. The heart is four-chambered and comprises the left atrium, right atrium, left ventricle, and right ventricle. The left and right sides of the heart are separated by a wall generally referred to as the septum. The native mitral valve of the human heart connects the left atrium to the left ventricle.

The atrioventricular valves (mitral and tricuspid) have a very different anatomy than other native heart valves. The mitral valve includes an annulus portion, which is an annular portion of the native valve tissue surrounding the mitral valve orifice, and a pair of cusps or leaflets extending downwardly from the annulus into the left ventricle. The mitral valve annulus can form a "D" shaped, oval, or otherwise out-of-round cross-sectional shape having major and minor axes. The anterior leaflet can be larger than the posterior leaflet, forming a generally "C"-shaped boundary between the abutting free edges of the leaflets when they are closed together. The leaflets are connected to the left ventricular wall at papillary muscles via chordae tendineae. Similarly, the tricuspid valve includes an annulus portion and three cusps, or leaflets, extending downwardly from the annulus, and connected to papillary muscles along the right ventricular wall through chordae tendineae. The chordae tendineae and papillary muscles are referred to as the subvalvular apparatus that facilitates the valve opening and closing during the cardiac cycle.

When the mitral valve is operating properly, the anterior leaflet and the posterior leaflet function together as a one-way valve to allow blood to flow only from the left atrium to the left ventricle. The left atrium receives oxygenated blood from the pulmonary veins. When the muscles of the left atrium contract and the left ventricle dilates (also referred to as "ventricular diastole" or "diastole"), the oxygenated blood that is collected in the left atrium flows into the left ventricle. When the muscles of the left atrium relax and the muscles of the left ventricle contract (also referred to as "ventricular systole" or "systole"), the increased blood pressure in the left ventricle urges the two leaflets together, thereby closing the one-way mitral valve so that blood cannot flow back to the left atrium and is instead expelled out of the left ventricle through the aortic valve. To prevent the two leaflets from prolapsing under pressure and folding back through the mitral annulus toward the left atrium, a plurality of fibrous cords, called chordae tendineae, tether the leaflets to papillary muscles in the left ventricle.

Mitral regurgitation occurs when the native mitral valve fails to close properly and blood flows into the left atrium from the left ventricle during the systolic phase of heart contraction. Mitral regurgitation is the most common form of valvular heart disease. There are many different causes of mitral regurgitation. One particular cause is excessive slack in at least one of the native leaflets. This excessive slack prevents the native leaflets from effectively closing during the systolic phase of heart contraction, thus allowing mitral regurgitation. In another case, the heart may have structural defects such that the leaflets are too far apart to provide sufficient coaptation of the leaflets to prevent flow to the left atrium during systole. In another case, the ventricle may be enlarged, pulling the leaflet coaptation edge away from the base too far below the annular plane towards the apex of the heart, preventing proper coaptation of the leaflets.

When the tricuspid valve is operating properly, the three leaflets function together as a one-way valve to allow blood to flow only from the right atrium to the right ventricle. The right atrium receives deoxygenated blood from the inferior and superior vena cava. When the muscles of the right atrium contract and the right ventricle dilates (during diastole), the deoxygenated blood that has collected in the right atrium flows into the right ventricle. When the muscles of the right atrium relax, and the muscles of the right ventricle contract (during systole), the increased blood pressure in the right ventricle urges the leaflets of the tricuspid valve together, thereby closing the one-way tricuspid valve so that blood cannot flow back into the right atrium, and is instead expelled out of the right ventricle through the pulmonary artery. Like the mitral valve, the tricuspid valve leaflets are tethered to papillary muscles in the right ventricle in order to prevent the leaflets from prolapsing under pressure and folding back through the tricuspid annulus toward the right atrium.

Tricuspid regurgitation occurs when the native tricuspid valve fails to close properly and blood flows into the right atrium from the right ventricle during the systolic phase of heart contraction. One cause of tricuspid regurgitation is an increase in the size of the right ventricle and dilation of the valve annulus such that the leaflets do not sufficiently coapt so as to prevent flow of blood to the right atrium during systole.

Various devices and methods for treating valvular regurgitation have been developed, including implanting a prosthetic valve (e.g., within the native mitral valve or the native tricuspid valve), surgically removing a portion of the native heart valve leaflets to reduce excessive slack, or clipping or otherwise coupling the leaflets to improve coaptation. These devices and methods can, however, be highly invasive, require lengthy or complex procedures, or require an extensive recovery period.

Thus, there is a continuing need for improved devices and methods for repairing native heart valve leaflets.

SUMMARY

Described herein are embodiments of a device that is primarily intended to be used to repair the leaflets of the mitral, aortic, tricuspid, or pulmonary heart valves, as well as methods for repairing the same. The device can be used to improve coaptation of heart valve leaflets.

In one representative embodiment, a leaflet capture device can include a first clip portion having an inner portion and an outer portion. The inner and outer portions can be configured to compress tissue of a first heart valve leaflet therebetween to secure the first clip portion to the first leaflet. The leaflet capture device can further include a second clip portion having an inner portion and an outer portion. The inner and outer portions can be configured to compress tissue of a second heart valve leaflet therebetween to secure the second clip portion to the second leaflet. The first and second clip portions can be configured to be separately deployable onto the first and second leaflets and secured to one another in vivo to bring portions of the first and second leaflets into closer proximity to each other, thereby improving coaptation of the first and second leaflets.

In some embodiments, the leaflet capture device can include a tether connecting the first and second clip portions.

In some embodiments, the inner portion of the first clip portion can include a first post. The inner portion of the second clip portion can include a coupling member for abutting the first post. In specific examples, the coupling member can include an annular base member and a second post. In a more specific example, the first post can be configured to abut the annular base member. In additional examples, the first post, the second post, the annular base member, or combinations thereof, can include a lumen for receiving the tether.

In some embodiments, the outer portion of the first or second clip portions, or both, can include a frame. When a clip portion includes a first post or a coupling member, the frame can be sufficiently spaced apart from the first post or the coupling member, respectively, such that a heart valve leaflet can be securely retained between a frame and the first post or the coupling member. In some examples, the frame can include resilient wing members, which can be configured to apply a compressive force to a heart valve leaflet. In another example, the first or second clip portions, or both, can include a first post or a second post, respectively, and the resilient wing members can be configured to compress a heart valve leaflet against a respective first or second post.

In further embodiments, the device can include a locking member configured to secure the first and second clip portions to one another. In some examples, when the device includes a tether, the locking device can include an aperture and can be used to secure the tether. In a more specific example, the tether can be secured relative to the locking member by reducing the size of the aperture such that sides of the aperture securely engage the tether. In further examples, the locking member can be coupled to the first or second clip portions, or both, such as the outer portion.

In some embodiments, the inner portion of each clip portion can include a coupling member and an inner frame member extending from the coupling member, and the outer portion of each clip portion can include an outer frame member that is biased toward the inner frame member. The outer frame member can include an engagement portion, which can include a plurality of retaining members, such as hooks or barbs. A tension member can extend through each of the coupling members and be secured thereto with a locking member on the tension member.

In a further embodiment, a clip portion can be used in combination with a delivery assembly that includes an actuating connector coupled to the outer frame member of the clip portion, such as being coupled to an engagement portion. The actuating connector can be selectively placed under tension to pull the outer frame member away from the inner frame member, thus facilitating placing a heart valve leaflet between the inner and outer frame members.

In a yet further embodiment, the device can include more than two clip portions, such as when the device is to be used to capture more than two leaflets, or when more than one clip portion is secured to a single leaflet.

In a further aspect, the present disclosure provides a method for improving coaptation of heart valve leaflets. The method can include delivering a first clip portion to a heart. The first clip portion can include an inner portion and an outer portion. The inner and outer portions can be configured to compress tissue of a first heart valve leaflet therebetween to secure the first clip portion to the first leaflet. A second clip portion can be delivered to the heart. The second clip portion can include an inner portion and an outer portion. The inner and outer portions can be configured to compress tissue of a second heart valve leaflet therebetween to secure the second clip portion to the second leaflet. The first clip portion can be secured to the first heart valve leaflet, and the second clip portion can be secured to the second heart valve leaflet. The first and second clip portions can be secured to one another to bring portions of the first and second leaflets into closer proximity to each other, thereby improving coaptation of the first and second leaflets.

In some embodiments, the first and second clip portions can be delivered separately to the heart.

In some embodiments, securing the first and second clip portions to one another can include engaging a locking member.

In some embodiments, securing the first and second clip portions to each other can include reducing slack in a tether connecting the first and second clip portions.

In some embodiments, the first and second clip portions are part of an above-described leaflet capture device.

In some embodiments, the first clip portion can include a coupling member, the second clip portion can include a post, and securing the first and second clip portions to one another can include abutting the post against the coupling member.

In some embodiments, securing a clip portion to its respective heart valve leaflet can include pulling the outer portion of the clip portion away from the inner portion and positioning the clip portion such that the respective heart valve leaflet is positioned between the inner and outer portions. In some implementations, the outer portion can be pulled using an actuating connector coupled to the outer portion and an element of a delivery assembly that can pull and release the actuating connector. The method can include repeatedly pulling and releasing the outer portion using the actuating connector to achieve a desired placement of the respective heart valve leaflet between the inner and outer portions.

In another aspect, the present disclosure provides an assembly that includes an elongate delivery catheter having at least one lumen and an above-described leaflet capture device.

The foregoing and other objects, features, and advantages of the invention will become more apparent from the following detailed description, which proceeds with reference to the accompanying figures.

BRIEF DESCRIPTION OF THE DRAWINGS

FIG. 2A is perspective view of the leaflet capture device of FIG. 1A, showing the locking member in a locked configuration.

FIG. 2B is an enlarged, perspective view of a portion of the leaflet capture device of FIG. 2A.

FIG. 10A is a perspective view of a delivery mechanism for the leaflet capture device of FIG. 8, such as for use in a retrograde delivery procedure.

FIG. 10B is a perspective view of a delivery mechanism for the leaflet capture device of FIG. 8, such as for use in an antegrade delivery procedure.

DETAILED DESCRIPTION

Described herein are embodiments of leaflet capture devices, such as leaflet clips, that are primarily intended to be used to improve coaptation of the leaflets of the mitral, aortic, tricuspid, or pulmonary heart valves, as well as methods for delivering the same. The leaflet capture devices can include multiple leaflet capture portions, each of which can be independently attached to one or more native heart valve leaflets. The leaflet capture portions can then be secured to one another. When the leaflet capture portions have been secured to one another, their associated native leaflets may be maintained in closer proximity, or brought in contact with, one another, thus improving coaptation of the leaflets. By improving coaptation, the leaflet capture devices can reduce or improve valvular regurgitation and, thus, improve the functionality of a defective heart valve. In some applications, the leaflet capture device can be implanted on prosthetic leaflets (or a combination of native and prosthetic leaflets), such as the leaflets of a prosthetic valve, to improve coaptation of the prosthetic leaflets.

In particular embodiments, a leaflet capture device can be configured to repair a native mitral valve leaflet. The leaflet capture device can access the mitral valve from the left ventricle and/or the left atrium in a minimally invasive manner (e.g., using a transcatheter technique). In further embodiments, a leaflet capture device can be configured to repair a native tricuspid leaflet. The leaflet capture device can access the tricuspid valve from the right ventricle and/or the right atrium in a minimally invasive manner (e.g., using a transcatheter technique).

Figure 1A:
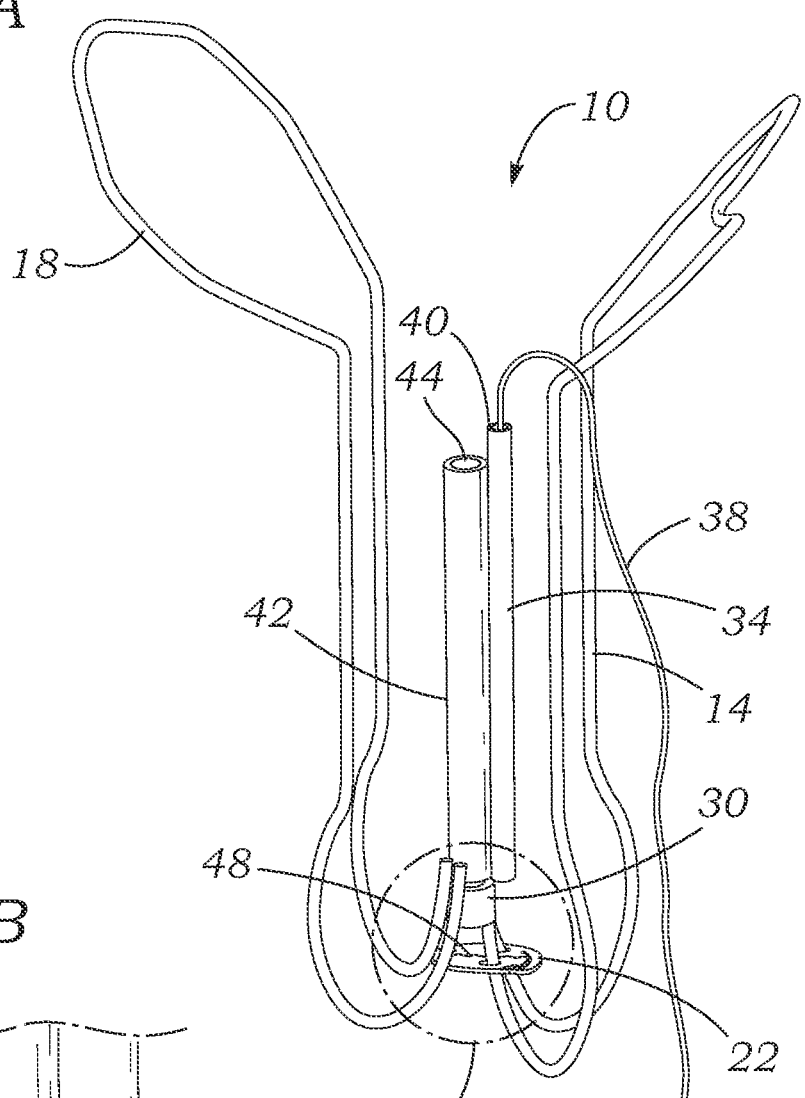
FIG. 1A is a perspective view of a representative embodiment of a leaflet capture device, with a locking member of the leaflet capture device in an unlocked configuration.
Figure 1B:
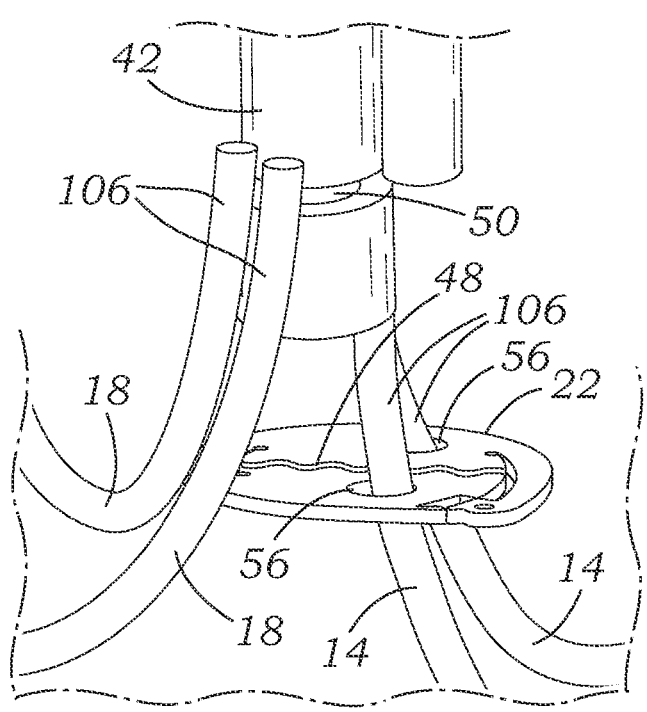
FIG. 1B is an enlarged, perspective view of a portion of the leaflet capture device of FIG. 1A.

Referring first to FIG. 1A and FIG. 1B, there is shown a representative embodiment of a leaflet capture device in the form of a leaflet clip assembly 10 for improving coaptation of native or artificial heart valve leaflets. The leaflet clip assembly 10 can include a first clip (or leaflet capture) portion 14, a second clip (or leaflet capture) portion 18, and a locking member 22. The first clip portion 14 can include an annular base member or ring 30 and a first post 34 secured to (e.g., by welding) and extending from the base member 30. A tension member or tether 38 can be coupled to an end 40 the first post 34 distal to the annular base member 30. The second clip portion 18 can include a second post 42 defining a lumen 44. The locking member 22 can define a seam or slit 48 for receiving the tension member 38.

The first clip portion 14 and the second clip portion 18 may be delivered to the heart as separate components, and assembled in vivo to produce the leaflet clip assembly 10. FIG. 1A shows the leaflet clip assembly 10 in a partially assembled state, where the first clip portion 14 and the second clip portion 18 are engaged by placing the second post 42 over the annular base member 30, such that the lumen 44 of the second post and a lumen 50 of the annular base member 30 are axially aligned. The assembly process can be completed by securing the first and second clip portions to each other to provide the fully assembled leaflet clip assembly 10, as further described below.

The locking member 22 can be coupled to the leaflet clip assembly 10. For example, the locking member 22 can include apertures 56 for receiving portions of a frame of the first clip portion 14 (shown in FIG. 1B) or portions of a frame of the second clip portion 18. With reference to FIG. 1B, the locking member 22 is shown in an unlocked state, with the slit 48 being sufficiently wide to allow the tension member 38 to move freely through the slit 48. In alternative embodiments, the locking member 22 can be secured to either the first clip portion 14 or the second clip portion 18 by any suitable technique or mechanism (e.g., welding, an adhesive, etc.).

After the first clip portion 14 and the second clip portion 18 have been deployed within the heart and placed against each other as shown in FIG. 1A, they can be secured together. With reference to FIGS. 2A and 2B, for example, the tension member 38 can be inserted through the lumen 44 of the second post 42, through the lumen 50 of the annular base member 30, and through the slit 48 of the locking member 22. After placing the tension member 38 under a desired degree of tension to secure the first clip portion 14 and second clip portion 18 to one another, the width of the slit 48 can be reduced such that the tension member is gripped and securely retained by the locking member 22, thereby securing the clip portions to each other and retaining the assembled state of the clip assembly 10.

Figure 3:
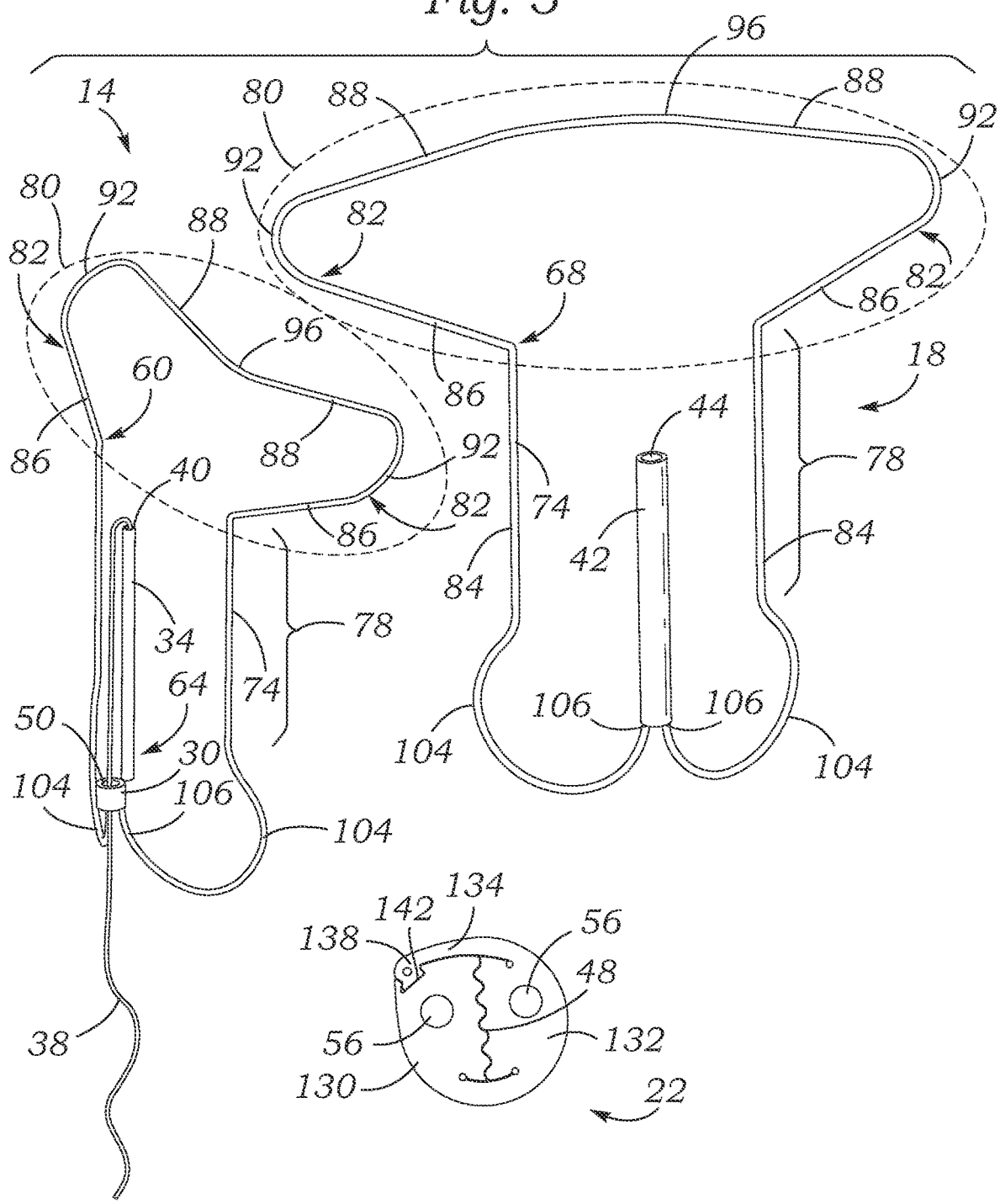
FIG. 3 illustrates the components of the leaflet capture device of FIG. 1A in a disassembled state, including perspective views of first and second clip portions of the leaflet capture device and a plan view of the locking member.

FIG. 3 illustrates the first clip portion 14, the second clip portion 18, and the locking member 22 in a disassembled state. The first clip portion 14 can include a frame 60 and a coupling member 64. In some cases, the frame 60 can be part of an outer portion of the first clip portion 14, and the coupling member 64 can be part of an inner portion of the first clip portion. The coupling member 64 can include the annular base member 30 and the first post 34. In some cases, the annular base member 30 and the first post 34 can be integrally formed, such as from a common piece of material (e.g., metal or plastic). In other cases, the annular base member 30 and the first post 34 can be joined together, such as by welding, brazing, adhering, or the like.

As noted above, the tension member 38 can be coupled an end 40 of the first post 34 distal to the annular base member 30. The tension member 38 can comprise, for example, an elongated, flexible piece of material, such as a suture, string, coil, cable, cord, wire, or similar material. In some cases, the tension member 38 can be joined to the first post 34 by welding, brazing, adhering, or the like. In other cases, the tension member 38 can be threaded through a lumen of the first post 34, and the proximal end of the tension member can be prevented from passing through the proximal end of the lumen. For example, the proximal end of the tension member 38 can be knotted to produce a bolus of material having a diameter larger than the diameter of the lumen of the first post 34, or the tension member 38 can be formed with, or coupled to, an enlarged member at its proximal end.

The lumen 50 of the base member 30 can have a suitably large diameter for receiving the tension member 38. In addition, the annular base member 30 can be sized and shaped to support the second post 42 in the manner shown in FIG. 2A when the leaflet clip assembly 10 is assembled. The annular base member 30 can be radially offset from the first post 34, such that the second post 42 can be placed on the annular base member 30 in an abutting relationship with the first post and second post located adjacent one another in parallel alignment as shown in FIG. 2A.

The second clip portion 18 can include a frame 68 and the second post 42. In some cases, the frame 68 can be part of an outer portion of the second clip portion 18, and the second post 42 can be part of an inner portion of the second clip portion. The lumen 44 of the second post can have a sufficiently large diameter for receiving the tension member 38. The second post 42 can have a diameter and/or thickness sufficiently large to abut, and be secured against, the annular base member 30.

In at least some implementations, the frames 60 and 68 can be at least generally similar. The frames 60, 68 can be formed from wire 74, such as a metal wire or a wire made from a biocompatible polymer. In at least certain examples, the wire 74 can be a sufficiently resilient material, such that the frames 60, 68 constructed therefrom can exert a compressive, retaining force when a heart valve leaflet is inserted between a frame and its respective post 34, 42. In addition, constructing the frames 60, 68 from a resilient and/or shape memory material can allow the first and second clip portions 14, 18 to be maintained in a radially compressed state during delivery to a heart and to self-expand when deployed from a delivery device inside the patient's body. In specific examples, the wire 74 used to form the frames 60, 68 can be made of a super-elastic shape memory material (such as Nitinol or another nickel-titanium alloy). In other examples, the wire 74 can be made of less elastic metals, such as stainless steel or cobalt chromium alloys, which in wire form can still exhibit sufficient shape memory and/or resiliency to enable the clip portions to be compressed to a smaller size for delivery and to self-expand when deployed inside the body.

The frames 60, 68 can each be configured to be secured against the outer surface of a heart valve leaflet (the inferior surface in the case of the mitral valve leaflets). In a particular example, the frame 60 of the first clip portion 14 can be configured to be secured against the inferior surface of the anterior mitral valve leaflet. The frame 68 of the second clip portion 18 can be configured to be secured against the inferior surface of the posterior mitral valve leaflet. If desired, the frame 60 and/or frame 68 can include retaining members, such as inwardly-extending hooks or barbs, which can be used to penetrate or otherwise engage the tissue of a heart valve leaflet.

Each frame 60, 68 can include a central longitudinal section 78 formed by substantially straight parallel segments 84 of the wire 74. Each frame 60, 68 can include a free end portion 80 having wings 82 that extend laterally and atrially away from respective segments 84 of the central longitudinal section 78. The segments of the wire 74 forming the free end portions 80 can be shaped (such as being bent) such that the free end portions are directed radially outwardly with respect to the plane of the respective central longitudinal section 78. That is, the free end portions 80 can bend radially outwardly relative to the first 34 or second posts 42, respectively.

Each of the wings 82 can include inner segments 86 and outer segments 88. Each of the inner 86 and outer segments 88 can be connected by an arcuate segment 92. The outer segments 88 of each wing 82 connect to each other at an apex 96. The outer segments 88 can be shaped, such as being bent, such that they extend toward or away from a respective post 34, 42. For example, in the illustrated embodiment the outer segments 88 of the first clip portion 14 can extend downwardly toward the post 34 to form a concave or inwardly bowed upper edge of the frame while the outer segments of the second clip portion 18 can extend upwardly away from the post 42 to form a convex or outwardly bowed upper edge of the second clip portion 18.

The opposite ends of the frames 60, 68 can include curved portions 104, each of which extends between a respective fixed end portion 106 and a respective intermediate segment 84. The fixed end portions 106 of each frame 60, 68 can extend downwardly away from a respective post 34, 42 and then transition into a corresponding curved portion 104, which can extend radially outwardly away from each other and then back toward each other and upwardly where the curved portions 104 transition into the intermediate segments 84. As best shown in FIGS. 2B and 3, the fixed end portions 106 of the frame 60 of the first clip portion 14 can be fixedly secured to the base member 30 of the frame, such as by welding, brazing, or use of an adhesive. Similarly, the fixed end portions 106 of the frame 68 of the second clip portion 18 can be fixedly secured to a lower end portion of the second post 42, such as by welding, brazing, or use of an adhesive.

The locking member 22 can be coupled to the fixed end portions 106 of the first or second frames 60, 68. In the illustrated embodiment, for example, as best shown in FIG. 2B, the end portions 106 of the frame 60 of the first clip portion 14 can extend through respective apertures 56 formed in the faces of the locking member 22, which can be disc-shaped. As best shown in FIG. 3, the slit 48 can extend radially for a portion of the diameter of the locking member so as to bisect the axial faces of the locking member 22 into first and second portions 130, 132, such as halves.

Figure 4:
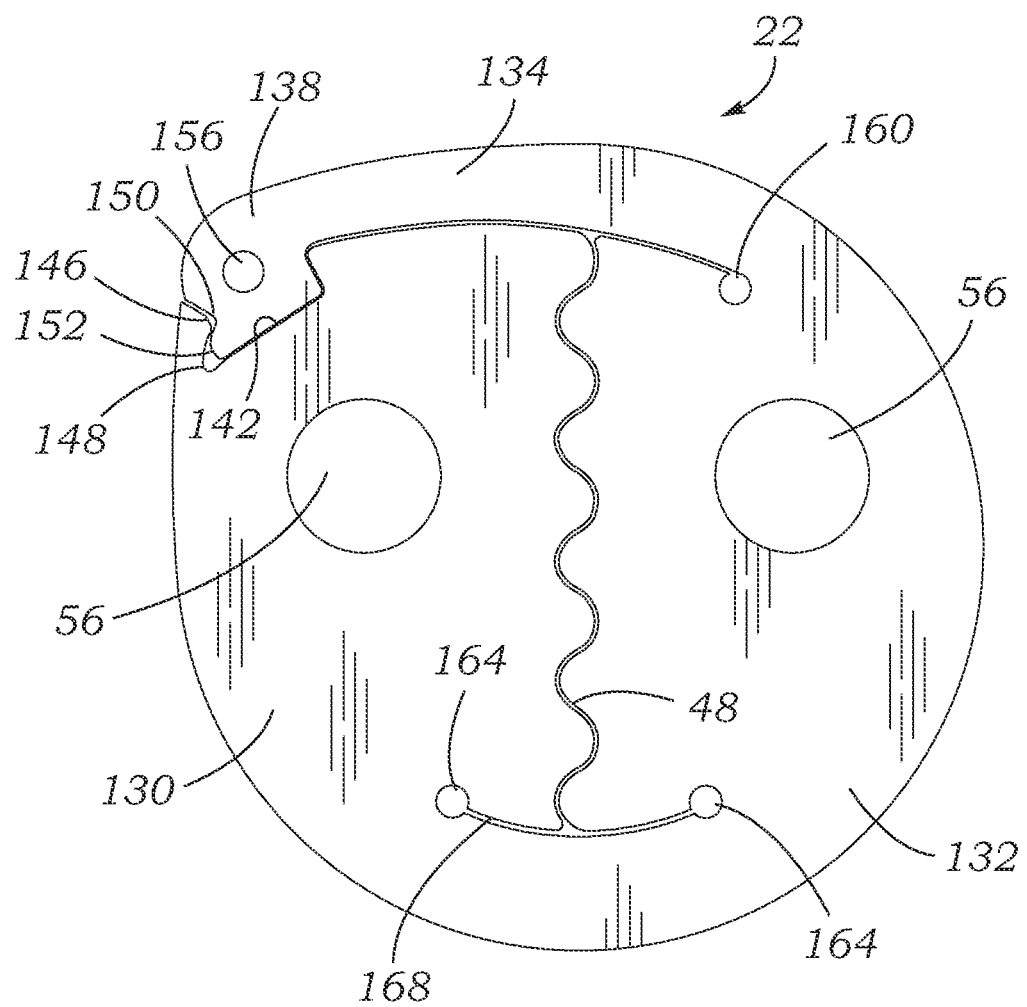
FIG. 4 is an enlarged, plan view of the locking member of FIG. 3.

With continued reference to FIG. 3, the locking member 22 can include a locking arm 134 formed along a portion of the perimeter of the locking member 22. The locking arm 134 can include a radially-inwardly extending tab 138 configured to be received by a mating notch 142 formed in the interior surface of the locking member 22. The locking arm 134 can flex or deform relative to the remaining portion of the locking member 22 to bring the tab 138 into and out of engagement with the notch 142. With additional reference to FIG. 4, a tongue 146 and a groove 148 can be formed on the radial surface of the notch 142. The tongue 146 and groove 148 can be received by a mating groove 150 and tongue 152 formed on an outer radial surface of the tab 138. By inserting the tongues 146, 152 into their respective grooves 148, 150, the tab 138 can be further locked into engagement within the notch 142. The tab 138 can include an aperture 156, which can receive a tool (e.g., a component of a delivery device) to help flex or deform the locking arm 134 when the tab 138 is to be inserted into, or released from, the notch 142. The width of the slit 48 can be reduced, such as to secure a length of the tension member 38, by inserting the tab 138 into the notch 142, with the tongues 146, 152 and grooves 148, 150 serving to prevent unintended release of the tab from the notch.

An opening 160 can be formed in the locking member 22 at the base of the locking arm 134. The opening 160 can help facilitate the locking arm 134 flexing radially outwardly, and the first and second portions 130, 132 moving apart from one another, increasing the width of the slit 48. Similarly, openings 164 can be formed at opposing ends of an arcuate cut or slit 168 formed at the end of the slit 48 opposite the notch 142. The openings 164 can facilitate the first and second portions 130, 132 flexing away from or towards one another, depending on whether the width of the slit 48 is to be increased or reduced.

The slit 48 can be used to secure the tension member 38. For example, when the leaflet clip assembly 10 is being implanted in a patient, the tab 138 can be disengaged from the notch 142, such that the slit 48 is sufficiently wide to permit free passage of the tension member 38 through the slit 48, as shown FIGS. 1A and 1B. When the first and second clip portions 14, 18 are to be secured together after deployment of the leaflet clip assembly 10 within the heart, the tab 138 can be inserted into the notch 142, drawing closed the slit 48, and securing the tension member 38 within it, as shown in FIGS. 2A and 2B.

In use, the first and second clip portions 14, 18 can be delivered in a disassembled state to the heart. However, the first and second clip portions 14, 18 can each be connected or coupled to the tension member 38 prior to insertion into the body. For example, the tension member 38 can be secured to the first post 34, threaded through the lumen 44 of the second post 42, through the lumen 50 of the annular base member 30, and through the slit 48 of the locking member 22. The locking member 22 can initially be in an unlocked state, such that the tension member 38 may move freely through the slit 48.

The first and second clip portions 14, 18 can be independently implanted onto their respective leaflets of the native valve. Once the first and second clip portions 14, 18 have been attached to their respective leaflets, the leaflet clip assembly 10 can be assembled within the heart by pulling the tension member 38 away from the leaflet clip assembly 10. As the tension member 38 is drawn through the lumen 44, the lumen 50, and the slit 48, the first and second clip portions 14, 18 are drawn together and brought into proximity such that the posts 34, 42 are in contact or in close proximity with respect to each other as shown in FIG. 2. When the first and second clip portions 14, 18 are sufficiently proximate one another, the second post 42 can rest on the annular base member 30. When a desired degree of tension has been applied to the tension member 38 to secure the first and second clip portions 14, 18 to one another, the tab 138 of the locking arm 134 can be inserted into the notch 142, reducing the width of the slit 48. The reduced width of the slit 48 causes opposing longitudinal edges of the slit to engage the tension member 38 and prevent movement of the tension member relative to the locking member 22.

Figure 5:
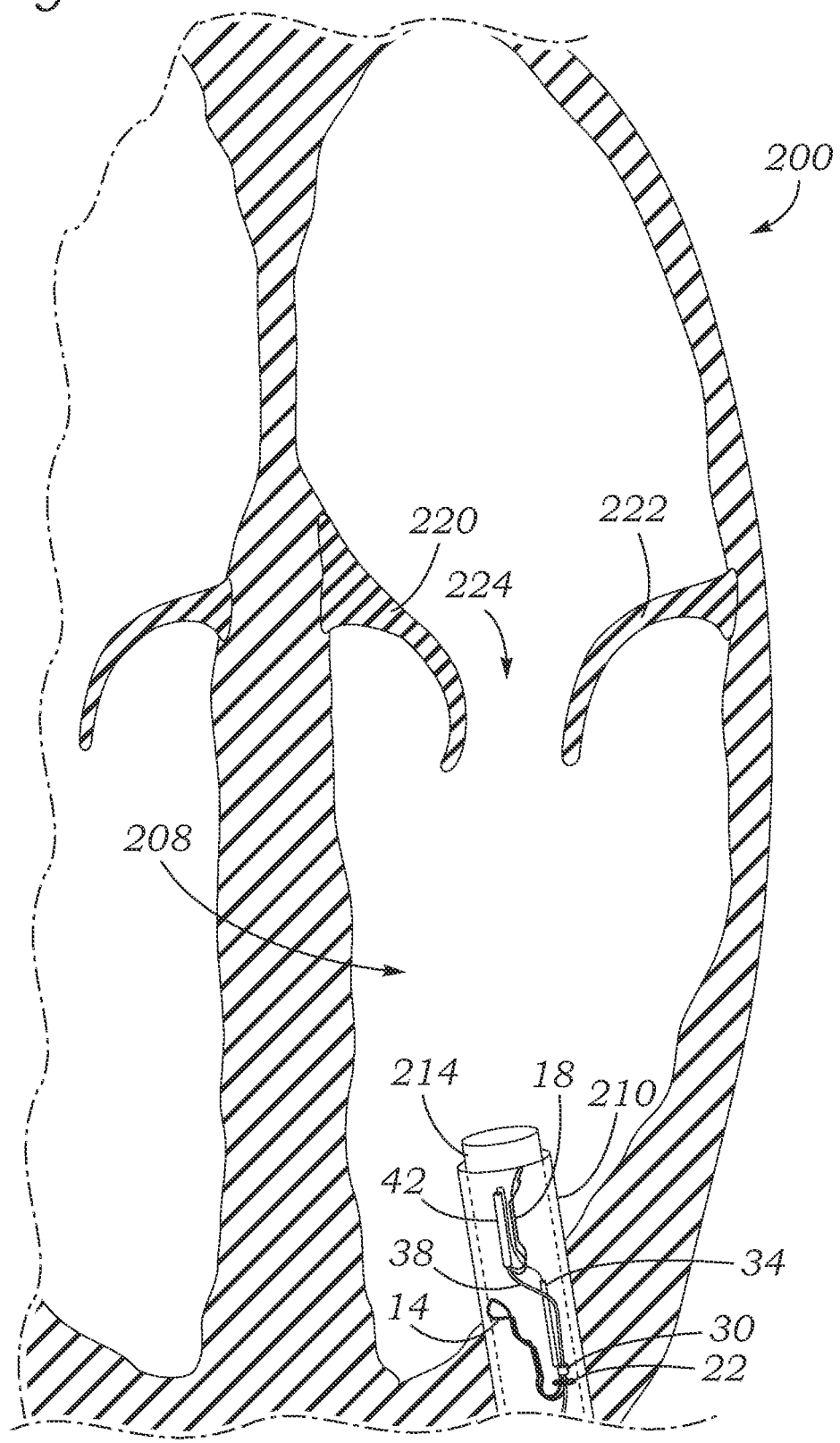
FIG. 5 is a cross section of the left atrium and the left ventricle of a heart, showing the delivery of the leaflet capture device of FIG. 1A in a disassembled state to the left ventricle.
Figure 6:
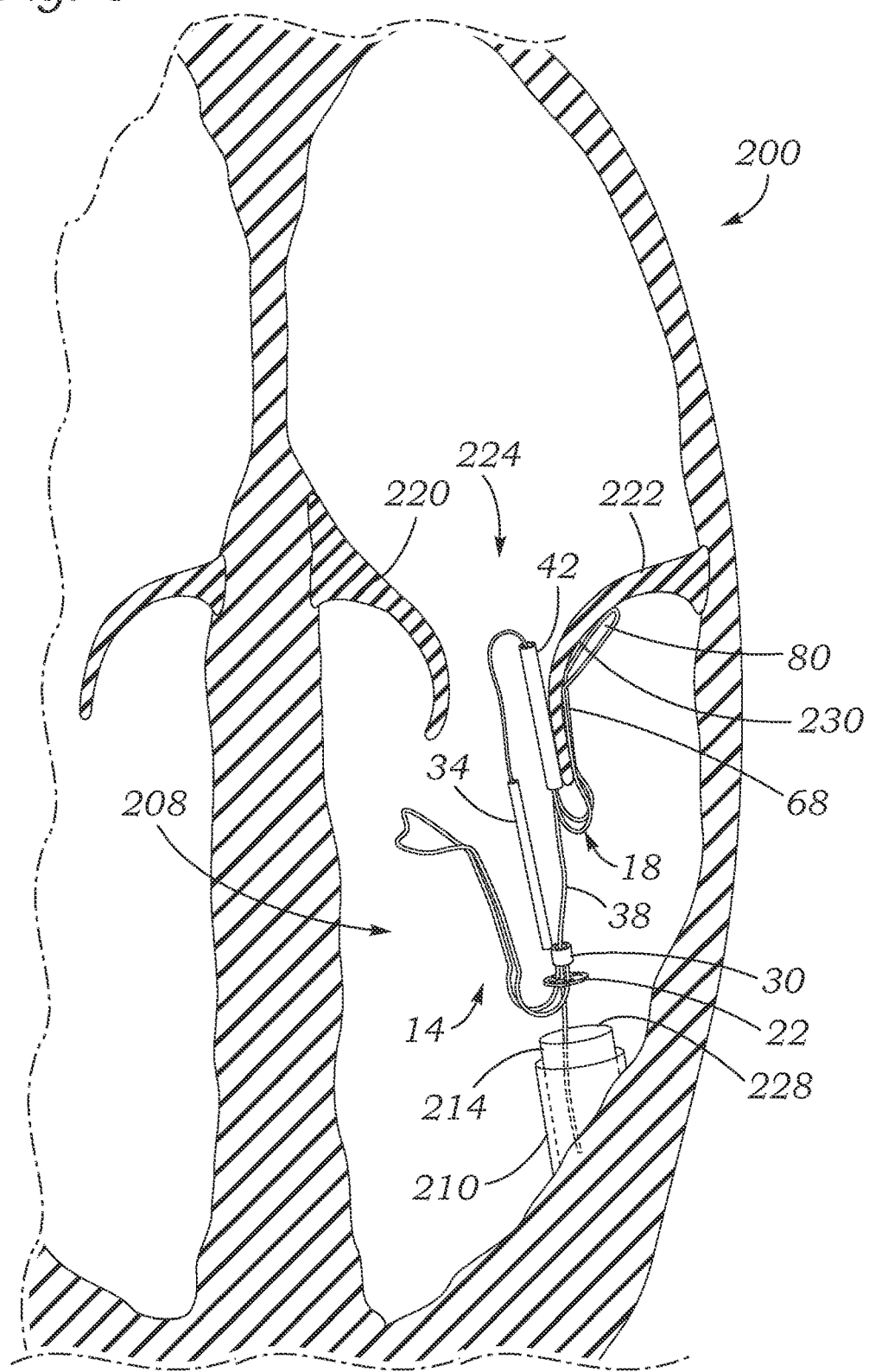
FIG. 6 is a cross section of the left atrium and the left ventricle of a heart, showing a first clip portion of the leaflet capture device of FIG. 1A engaging the posterior mitral valve leaflet and coupled to a second clip portion by a tension member.
Figure 7:
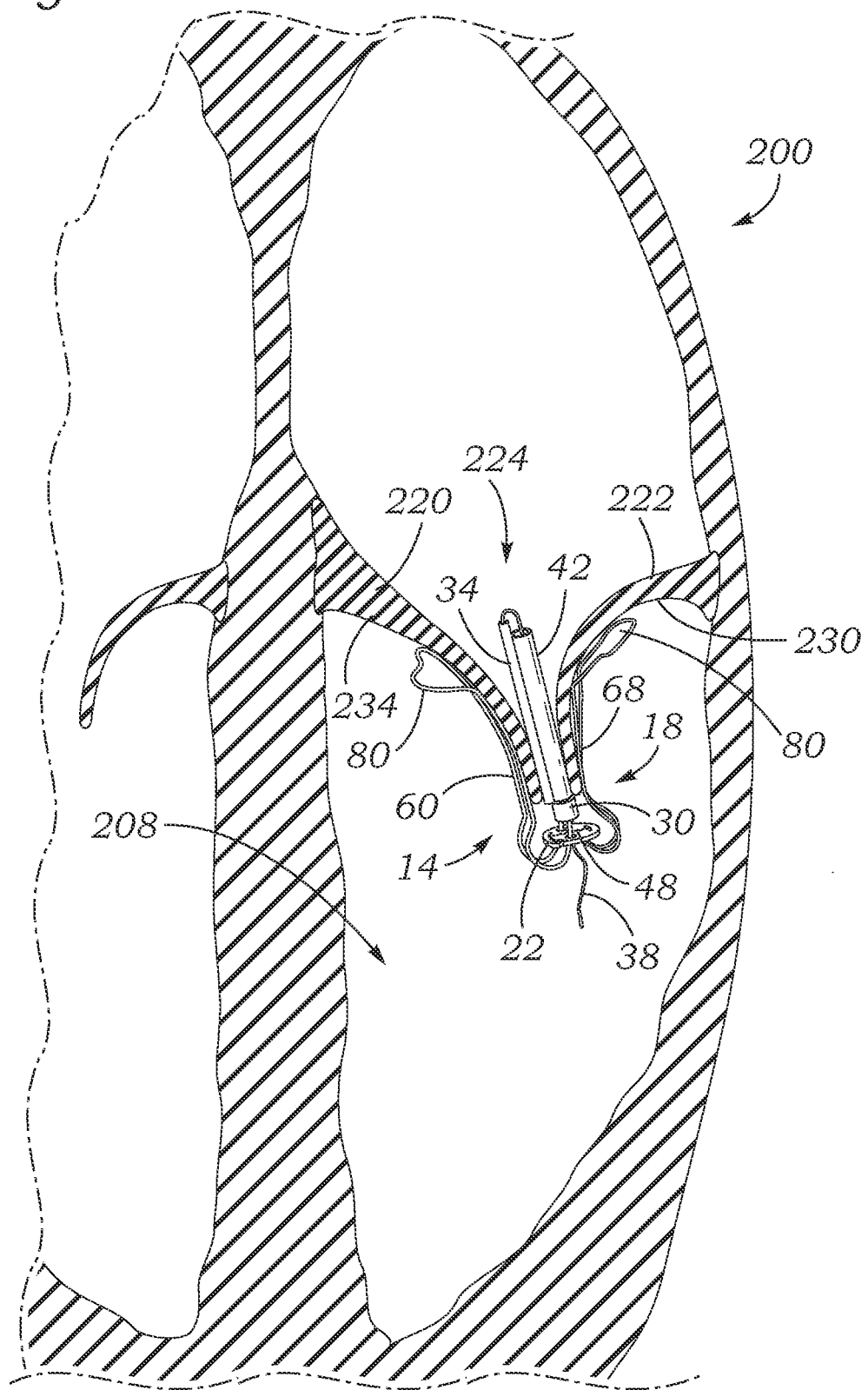
FIG. 7 is a cross section of the left atrium and the left ventricle of a heart, showing the leaflet capture device of FIG. 1A in an assembled state, with a first clip portion of the leaflet capture device engaging the posterior mitral valve leaflet and a second clip portion of the leaflet capture device engaging the anterior mitral valve leaflet.

FIGS. 5-7 illustrate an example method for delivering the leaflet clip assembly 10 into a patient's heart and assembling the leaflet clip assembly in vivo, including attaching the leaflet clip assembly 10 to the mitral valve leaflets in order to improve coaptation of the leaflets and reduce regurgitation of the mitral valve. With reference first to FIG. 5, using a transventricular procedure, a surgical incision can be made in the chest and on the bare spot on the lower anterior ventricular wall. A delivery or introducer catheter 210 (also referred to as an "introducer") can be advanced through the incision on the anterior ventricular wall and into the left ventricle 208 of a heart 200. A deployment catheter 214 can be advanced within a lumen of the delivery catheter 210 and into the left ventricle 208. The first clip portion 14 and the second clip portion 18 of the leaflet clip assembly 10 can be advanced through the deployment catheter 214 in a dissembled state. For example, the first and second clip portions 14, 18 can be advanced using a pushing device or other advancement mechanism. Alternatively, the first and second clip portions 14, 18 can be pre-loaded in the distal end portion of the delivery catheter and delivered into the heart by advancing the deployment catheter 214 through the introducer catheter 210.

In the illustrated example, the second clip portion 18 is positioned distally relative to the first clip portion 14 within the deployment catheter 214 so that the second clip portion is deployed and fastened to a leaflet before the first clip portion. In other implementations, the first clip portion 14 can be positioned distally relative to the second clip portion 18 within the deployment catheter 214 so that the first clip portion is deployed and fastened to a leaflet before the second clip portion.

Although the first and second clip portions 14, 18 can be delivered in a disassembled state, the tension member 38 can be positioned with respect to the first and second clip portions so as to aid in capturing of the anterior mitral valve leaflet 220 and the posterior mitral valve leaflet 222 of the mitral valve 224 by the first and second clip portions, and to facilitate subsequent assembly of the leaflet clip assembly 10. For instance, the tension member 38 can have a distal end secured to the first post 34 of the first clip portion 14 and extending from the first post through the lumen 44 of the second post 42 of the second clip portion 18. The tension member 38 can also extend through the lumen 50 of the annular base member 30 of the first clip portion 14, through the slit 48 of the locking member 22, and then proximally through the lumen of the deployment catheter 214. The proximal end of the tension member 38 can extend outside the patient's body for manipulation by the user.

Referring now to FIG. 6, the first and second clip portions 14, 18 can be advanced from the distal opening 228 of the deployment catheter 214 and into the left ventricle 208. The second clip portion 18 can be deployed onto the posterior mitral valve leaflet 222 such that a portion of the posterior mitral valve leaflet 222 is held between the frame 68 of the second clip portion 18 and the second post 42. As described with respect to FIG. 3, the upper, free end portion 80 of the frame 68 can exert a spring-like, compressive force against the inferior surface 230 of the posterior mitral valve leaflet 222, helping to maintain engagement of the posterior mitral valve leaflet with the second post 42. The second clip portion 18 can be configured to clip or clamp tissue of the native leaflet 222 with sufficient force such that the second clip portion can anchor itself onto the native leaflet 222 prior to being secured to the first clip portion. In addition, the shape of the frame 68 can enhance contact of the second clip portion 18 with the posterior mitral valve leaflet 222.

With reference to FIG. 7, the first clip portion 14 can be deployed onto the anterior mitral valve leaflet 220. In at least some cases, the tension member 38 can be pulled proximally to remove slack in tension member between the locking member 22 and the first post 34. In this way, the first and second clip portions 14 and 18 can be moved into engagement, as well as moving the first clip portion 14 superiorly, helping it engage the anterior mitral valve leaflet 220.

A portion of the anterior mitral valve leaflet 220 is held between the frame 60 and the first post 34. As with the second clip portion 18, the upper, free end portion 80 of the frame 60 of the first clip portion 14 can exert a spring-like, compressive force against the inferior surface 234 of the anterior mitral valve leaflet 220, helping to maintain engagement of the anterior mitral valve leaflet with the first post 34. The first clip portion 14 can be configured to clip or clamp tissue of the native leaflet 220 with sufficient force such that the first clip portion can anchor itself onto the native leaflet 220 prior to being secured to the second clip portion 18. The shape of the frame 60 can provide significant contact between the frame and the anterior mitral valve leaflet 220.

As the first clip portion 14 is moved superiorly, the annular base member 30 can be positioned inferiorly to the second post 42, eventually abutting the base of the second post as the tension member 38 is drawn through the lumen 44 of the second post, the lumen 50 of the annular base member, and the slit 48 of the locking member 22. As the first and second clip portions 14, 18 are brought into engagement with each other, the native leaflets 220, 222 are brought into closer proximity, or in contact, with each other to improve coaptation of the leaflets. When a desired degree of tension has been applied to the tension member 38, the tension member can be secured by inserting the tab 138 of the locking arm 134 of the locking member 22 into the notch 142. The tension member 38 can be severed at a point within the left ventricle, typically proximate the inferior surface of the locking member 22. The distal end of the severed tension member 38 can be retracted into the deployment catheter 214, and the deployment catheter and the delivery catheter 210 removed from the heart 200.

It should be appreciated that the leaflet clip assembly 10 can be delivered to, and assembled within, the heart in a different manner than that depicted in FIGS. 5-7. For example, although FIGS. 5-7 illustrate the second clip portion 18 being attached to the posterior mitral valve leaflet 222 before the first clip portion 14 is attached to the anterior mitral valve leaflet 220, in other cases, the first clip portion 14 may be attached to the anterior mitral valve leaflet 220 before the second clip portion 18 is attached to the posterior mitral valve leaflet 222. Additionally, although the first and second clip portions 14, 18 are described as being coupled to the posterior and anterior mitral valve leaflets 222, 220, respectively, in other aspects, the first clip portion 14 may be implanted on the posterior mitral valve leaflet and the second clip portion 18 may be implanted on the anterior mitral valve leaflet. In a further aspect, each of the first and second clip portions 14, 18 may be implanted on both the anterior and posterior mitral valve leaflets, such as being positioned proximate the leaflet commissures.

The locking member 22 can be a suture clip, or another type of fastener that can be deployed from a catheter and secured to a suture within the patient's body. Various suture clips and deployment techniques for suture clips that can be used in the methods disclosed in the present application are disclosed in U.S. Publication Nos. 2014/0031864 and 2008/0281356, and U.S. Pat. No. 7,628,797, which are incorporated herein by reference. In some embodiments, the locking member 22 can be configured such that the tension member 38 can be pulled through the slit 48 of the locking member 22 when bringing the clip portions 14, 18 into engagement with each other, and the portions 130, 132 of the locking member resist movement of the tension member through the slit 48 in the opposite direction to maintain tension on the tension member.

In further implementations, the tension member 38 can be secured in another manner by delivering the locking member separately from the clip portions 14, 18. For example, the leaflet clip assembly 10 may be secured to the mitral valve 224 generally as described in conjunction with FIGS. 5-7. Once a desired degree of tension has been applied to the tension member 38, the locking member, or a similar retention member, suture clip or fastener, may be advanced along the tension member 38 (after being deployed from the catheter 214 or another delivery device) and secured proximate the inferior surface of the annular base member 30. Additionally, although FIGS. 5-7 describe a transventricular procedure, the leaflet clip assembly 10 can be delivered to the heart in another manner. For example, rather than being delivered through the left ventricle, the leaflet clip assembly 10 can be delivered through the left atrium. In some implementations, the leaflet clip assembly 10 can be delivered transseptally by advancing the deployment catheter 214 though the inferior or superior vena cava, into the right atrium, across the atrial septum, and into the left ventricle 208. Attaching the first and second clip portions 14, 18 to the leaflets 220, 222 can proceed analogously to the procedure described in conjunction with FIGS. 5-7.

In other embodiments, the locking member 22 can be omitted and the clip portions 14, 18 can have respective locking features that engage and lock each other when brought into contact with each other. For example, a portion of the first post 34 can have a locking feature that forms a snap-fit connection with a corresponding locking feature on the second post 42 when the clip portions are brought into contact with each other.

In other cases, the attachment or assembly procedures can vary. For example, rather than pulling the tension member 38 inferiorly, toward the bottom of the heart, the leaflet clip assembly 10 can be assembled using a superiorly directed force, toward the top of the heart. In a specific example, the tension member 38 can pass from the base of the second post 42, through the lumen 44, and out from the top of the second post. The annular base member 30 can be urged beneath the second post 42 by applying a superiorly directed force to the tension member 38. When a desired degree of tension has been applied, the locking member 22, or another retention member or fastener, such as a suture clip, can be advanced over the tension member 38 proximate the top of the second post 42.

Figure 8:
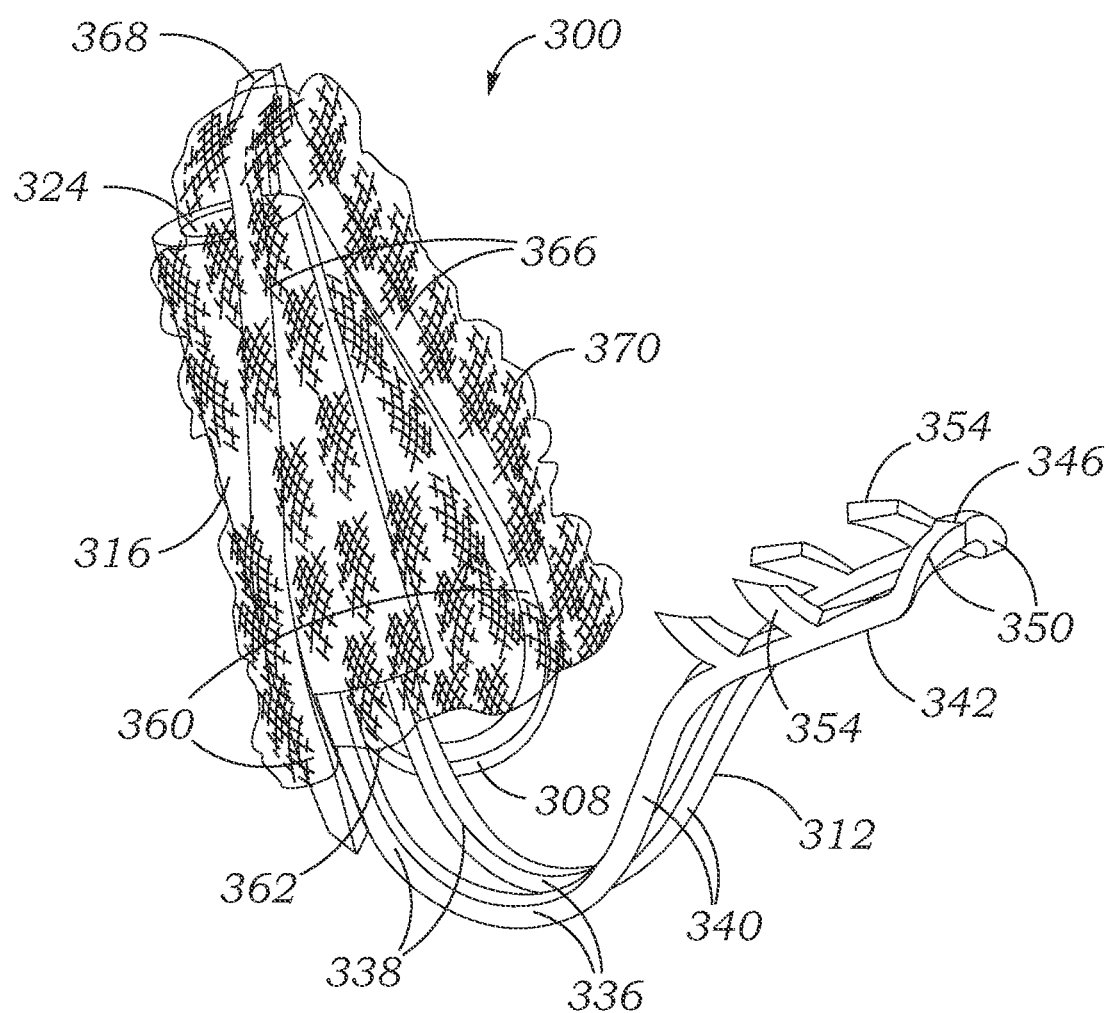
FIG. 8 is a perspective view of another representative embodiment of a leaflet capture device that can secure a heart valve leaflet between an outer member and an inner member.

FIG. 8 illustrates another embodiment of a leaflet capture portion or clip portion 300 that can be used with one or more other clip portions of the same or similar type to form a leaflet repair device or clip assembly. The clip portion 300 can include an inner frame member 308 and an outer frame member 312. The inner member 308 and the outer member 312 can each be coupled to a coupling member 316. The coupling member 316, can be used, for example, to attach the clip portion 300 to another clip portion.

In some cases, two or more of the inner member 308, the outer member 312, and the coupling member 316 can be of a unitary construction, such as being cut or machined from a single piece of material. In other cases, one or more of the inner member 308, the outer member 312, and the coupling member 316 can be coupled together, such as by welding, brazing, or the use of an adhesive.

The coupling member 316 can be tubular or cylindrical, defining a lumen 324. The lumen 324 may be configured to receive a tension member 328 (shown in FIG. 9). The tension member 328 can comprise, for example, an elongated, flexible piece of material, such as a suture, string, coil, cable, cord, wire, or similar material. The tension member 328 can extend through opposing ends of the lumen 324 and be secured by a locking member 332 (FIG. 9), such as a suture clip, or another type of fastener that can be deployed from a catheter and secured to a suture within a patient's body. In at least some aspects, the locking member 332 can be configured analogously to the locking member 22.

In the embodiment of FIG. 8, the outer member 312 is shown as a pair of elongate frame portions 336 extending axially from a bottom portion of the coupling member 316. The frame portions 336 can curve convexly, transitioning from downwardly directed portions 338 to upwardly directed portions 340. An engagement section 342 can be formed by outwardly bowed portions of the frame portions 340. The frame portions 340 can be connected to an outermost segment 346 of the outer member 312. The outermost segment 346 can be perpendicular to the frame portions 340, and can include arcuate, concave portions 350.

A plurality of tissue-engaging members 354 can extend inwardly from the frame portions 340 of the engagement section 342. The members 354 can be, for example one or more hooks or barbs configured to engage and/or penetrate the tissue of a heart valve leaflet. The number, size, length, shape, and distribution of the tissue-engaging members 354 can be selected to provide a desired degree of securement to a heart valve leaflet. For example, longer, sharper, and more numerous tissue-engaging members 354 can provide for stronger engagement with a heart valve leaflet.

In some aspects, at least a portion of the outer member 312, such as the frame portions 336, can be formed from a resilient material, such as a metal, a biocompatible polymer, or another type of biocompatible material. In specific examples, the resilient material can be in the form of a wire. The material from which the frame portions 336 is constructed is typically selected to be sufficiently resilient such that the outer member 312 (and more particularly the engagement section 342) can exert a compressive, retaining force when a heart valve leaflet is inserted between the outer member 312 and the inner member 308.

In addition, constructing the frame portions 336 from a resilient and/or shape memory material can allow the engagement portion 342 to be pulled or deflected away from the inner member 308 during deployment of the clip portion 300 in order to facilitate placing a leaflet between the inner member and the engagement portion of the outer member 312. The engagement portion 342 can then revert back to its non-deflected state under its own resiliency to compress the leaflet between the engagement portion and the inner member 308, and optionally engage the tissue-engaging members 354 with the tissue of the heart valve leaflet. In specific examples, the frame portions 336 can be constructed from a super-elastic shape memory material (such as Nitinol or another nickel-titanium alloy).

In other examples, the frame portions 336 can be made of less elastic metals, such as stainless steel or cobalt chromium alloys, which can still exhibit sufficient shape memory and/or resiliency and/or flexibility to enable the engagement portion 342 to be pulled away from the support member 308 during delivery, and then return to, or be manipulated to, a closed position after leaflet capture. In some cases, a clip portion 300 can be deployed with the engagement portion 342 in an open position, and the engagement portion can be manipulated (e.g., pushed or pulled) to, or released to resume, a closed position after leaflet capture.

The inner member 308 can include a pair of elongate support frame members 360 extending axially from the bottom portion of the coupling member 316, being coupled to (or extending from) a portion of the coupling member radially outwardly with respect to where the frame portions 336 adjoin the coupling member 316. The support frame members 360 can curve convexly, transitioning from downwardly directed portions 362 to upwardly directed portions 366. The upwardly directed portions 366 of the support frame members 360 can curve inwardly towards one another, meeting (including, in at least some cases, being of unitary or contiguous construction) at an uppermost segment 368. In some aspects, the uppermost segment 368 can be arcuate, such as being concave.

The upwardly directed portions 366 of the support frame members 360 can be positioned adjacent to the outer axial surface of the coupling member 316. In some cases, the upwardly directed portions 366 of the support frame members 360 can be coupled to the coupling member 316, such as by welding, brazing, or the use of an adhesive. In other cases, the upwardly directed portions 366 of the support frame members 360 can abut the outer axial surface of the coupling member 316.

The inner member 308 and the coupling member 316 can be covered with a biocompatible covering 370. For example, the covering may be a cloth or fabric material (e.g., a PET fabric). The biocompatible covering 370 may buffer leaflet tissue from contact with the support member 308, and increase the surface area of the clip portion 300 in contact with the leaflet, which can help secure the leaflet to the clip portion. Similarly, in some cases, the material used for the biocompatible covering 370 can be selected to provide a desired degree of frictional or other retaining force. In some embodiments, the outer member 312 also can be covered with a similar biocompatible cloth or fabric covering.

Figure 9:
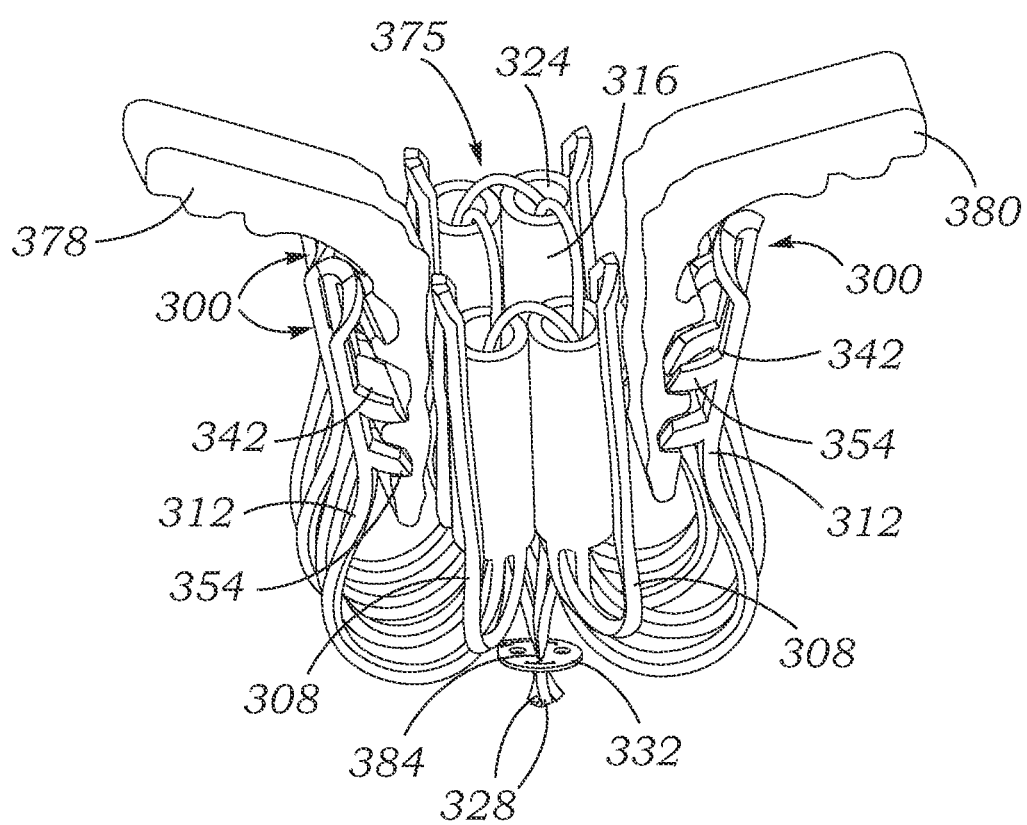
FIG. 9 is a perspective view of a plurality of leaflet capture devices of the type shown in FIG. 8 implanted on the leaflets of the native mitral valve.

FIG. 9 illustrates how the leaflet clip portion 300 of FIG. 8 may be used with other clip portions 300 to form a leaflet repair device or clip assembly 375 to improve cooptation of heart valve leaflets. Specifically, FIG. 9 illustrates four clip portions 300 being used to form the clip assembly 375 to improve coaptation of the anterior mitral valve leaflet 378 and the posterior mitral valve leaflet 380. Although four clip portions 300 are shown in the assembly 375, a greater or fewer number of clip portions could be used to form an assembly. For example, a clip assembly 375 can include two clip portions 300, similar to clip assembly 10. Typically, although not necessarily, an assembly includes at least one clip portion 300 for each leaflet 378, 380.

As further described below, a single clip portion 300 can be secured to multiple leaflets to improve leaflet coaptation, and thereby function as a leaflet repair device without being secured to additional clip portions to form an assembly. In some cases, a clip assembly can include the same number of clip portions 300 mounted on each leaflet 378, 380 (e.g., two on each leaflet in the illustrated example), while in other cases the number of clip portions 300 mounted on each leaflet can differ. The number and positioning of the clip portions 300 on the leaflets 378, 380 can be selected to apply a desired coaptive force to the leaflets, which can be symmetrical or unsymmetrical, depending on the desired result.

Each clip portion 300 can be secured to another clip portion using one or more tension members 328, (e.g., suture material), with at least one tension member being wound through the coupling members 316 of pairs of adjacent clip portions 300, including both anteriorly and posteriorly adjacent clip portions, and medially and laterally adjacent clip portions. The ends of the tension member 328 can be gathered and retained using the locking device 332, such as the slit 384 of a suture clip 332.

In some aspects, a single clip portion 300 can be secured to two or more leaflets, without being secured to additional clip portions, to improve leaflet coaptation. In other words, the single clip portion 300 can be secured to the leaflets by placing adjacent edges of two or more leaflets between the inner member 308 and the outer member 312. The clip portion 300 is held in place by compressive forces between its inner member 308 and the engagement portion 342 of its outer member 312, as well as the tissue engaging members 354 of the engagement portion.

In the assembly of FIG. 9, each of the clip portions 300 can retain the tissue of its respective leaflet 378, 380 between the engagement portion 342 of its outer member 312 and its inner member 308. The leaflets 378, 380 can be retained by their respective clip portions 300 at least in part through a compressive force. Additionally, the clip portions 300 can be further secured to the leaflets 378, 380 through the tissue-engaging members 354, which can protrude into the leaflet tissue. Although not shown in FIG. 9, the inner members 308, the coupling members 316, and/or the outer members 312 can be covered by the biocompatible cover 370 shown in FIG. 8.

FIG. 10A illustrates a delivery assembly 400 that can be used to deliver a clip portion 300 to the heart for deployment, such as using a retrograde approach (e.g., transfemorally, transventricularly, transaortically, or transapically), beneath the mitral valve. The delivery assembly 400 can include an outer delivery catheter 404. An inner support catheter 408 can be disposed within a lumen of a deployment catheter 416. In turn, a guide wire 412 can extend through and axially beyond the inner support catheter 408. The guide wire 412 can pass through the lumen of the coupling member 316 of a clip portion 300.

An actuating connector 420 can be coupled to a distal end of the deployment catheter 416 and the engagement portion 342 of the clip portion 300. The connector 420 can be, for example, a flexible piece of material, such as a length of suture material, or can be a more rigid component, such as metal rod or strut. The delivery catheter 404, inner support catheter 408, guide wire 412, and deployment catheter 416 may be moved axially distally and proximally with respect to one another to facilitate deployment of the clip portion 300, including capturing of a leaflet between the engagement portion 342 and the inner member 308.

After advancing the delivery catheter 404 into the left ventricle, the clip portion 300 can be advanced through the distal opening of the delivery catheter over the guide wire 412 to a position beneath a mitral valve leaflet. The clip portion 300 can be advanced by urging the clip portion distally using the inner support catheter 408 toward the inferior surface of the leaflet. When the clip portion 300 is sufficiently proximate the leaflet, the engagement portion 342 of the clip portion can be pulled downwardly, toward the distal end of the delivery catheter 404, by pulling the deployment catheter 416 proximally relative to the inner support catheter 408. This causes the actuating connector 420 to be placed under tension, thus pulling the engagement portion 342. Pulling the engagement portion 342 toward the distal end of the delivery catheter 404 increases the separation between the engagement portion 342 and the inner member 308 of the clip portion 300, facilitating insertion of a leaflet therebetween.

When the leaflet is at a desired position between the inner member 308 and the engagement portion 342, the deployment catheter 316 can be moved distally with respect to the inner support catheter 408, releasing tension on the actuating connector 420. The release of tension allows the engagement portion 342 to return to its unstressed or undeflected configuration under its own resiliency, reducing the separation between the engagement portion and the inner member 308 to secure the leaflet therebetween. The tissue-engaging members 354 of the clip portion 300 can engage the tissue of the heart valve leaflet to help secure the clip portion to the leaflet.

During implantation, if the physician desires to adjust the position of the clip portion 300 with respect to the leaflet, the physician can again move the deployment catheter 416 distally to open the clip portion, and then move the deployment catheter proximally to close the clip portion and secure the leaflet. During this process of opening and closing the clip portion 300 (increasing and decreasing the separation between the engagement portion 342 and the inner member 308), the inner support catheter 408 can have sufficient rigidity to counter the pulling force exerted by the actuating connector 420, thus allowing the engagement portion 342 to be pulled toward the delivery catheter 404, rather than bending the clip portion 300, guide wire 412, and inner support catheter 408 outwardly.

This implantation process can be repeated for one or more additional clip portions 300, at least one being attached to another of the heart valve leaflets. After the clip portions 300 have been secured to a respective leaflet, one or more lines of suture 328 (FIG. 9) can be threaded through the coupling members 316 of the clip portions, placed under a desired degree of tension to bring the clip portions together to form an assembly (e.g., the assembly 375) and improve leaflets coaptation, and the free suture ends secured by the locking member 332 (FIG. 9). Alternatively, suture 328 can be pre-threaded through the coupling members 316 of the clip portions 300 prior to deployment within the heart. The clip portions 300 can be secured to their respective leaflets as previously described, the suture 324 placed under a desired degree of tension, and the free suture ends secured by the locking member 332. When the clip portions 300 have been appropriately positioned, the actuating connector 420 can be cut or removed, and the delivery assembly 400 removed from the patient.

FIG. 10B illustrates a delivery assembly 440 that can be used to deliver a clip portion 300 to the heart for deployment, such as using an antegrade approach (e.g., transfemorally, or transseptally) to deliver the clip portion above the mitral valve. The delivery assembly 440 can include an outer delivery catheter 444. An inner support catheter 448 can be disposed within a lumen of the delivery catheter 444. An inner shaft or control wire 452 can be disposed within a lumen of the inner support catheter 448. The inner shaft 452 can pass through the lumen of the coupling member 316 of the clip portion 300. In some embodiments, the inner shaft 452 can have a lumen to receive a guide wire.

An actuating connector 456 can be coupled to a distal end of the inner shaft 452, distal to the bottom of the coupling member 316. The actuating connector 456 can be coupled to the engagement portion 342 of the clip portion 300. The delivery catheter 444, inner support catheter 448, and inner shaft 452 can be moved axially distally and proximally with respect to one another to facilitate deployment of the clip portion 300, including capturing of a leaflet between the engagement portion 342 and the support member 308.

After advancing the delivery catheter 444 into the left atrium, the clip portion 300 can be advanced through the distal opening of the delivery catheter to a position beneath a mitral valve leaflet. The clip portion 300 can be advanced by urging the clip portion distally using the inner support catheter 448 toward the inferior portion of the left ventricle. When the clip portion 300 is sufficiently proximate the leaflet, the engagement portion 342 of the clip portion can be pulled downwardly, toward the inferior surface of the left ventricle, and away from the distal end of the delivery catheter 344, by pushing the inner shaft 452 distally relative to the inner support catheter 448.

The clip portion 300 can be releasably coupled to the inner support catheter 448 such that the clip portion 300 does not move axially when the inner shaft 452 is moved within the inner support catheter. Pushing the inner shaft 452 causes the actuating connector 456 to be pulled and placed under tension, pulling the engagement portion 342 towards the inferior surface of the left ventricle, and increasing the separation between the engagement portion and the inner member 308 of the clip portion 300. This increased separation can facilitate the insertion of a leaflet therebetween.

The inner support catheter 448 and the inner shaft 452 can be pulled proximally, capturing the leaflet between the engagement portion 342 and the inner member 308. When the leaflet is at a desired position between the inner member 308 and the engagement portion 342, the inner shaft 452 can be moved proximally relative to the inner support catheter 448, releasing tension on the actuating connector 456, and allowing the engagement portion 342 to return to its unstressed configuration under its own resiliency. The unstressed configuration can have reduced separation between the engagement portion and the inner member 308, thus securing the leaflet therebetween. The retaining members 354 of the clip portion 300 can engage the tissue of the heart valve leaflet to help secure the clip portion to the leaflet.

During implantation, if the physician desires to adjust the position of the clip portion 300 with respect to the leaflet, the physician can again move the inner shaft 452 distally relative to the inner support catheter 448 to open the clip portion, and then move the inner shaft 452 proximally to close the clip portion and secure the leaflet. During this process of opening and closing the clip portion 300, the inner support catheter 448 can have sufficient rigidity to counter the pulling force exerted by the actuating connector 456, thus allowing the engagement portion 342 to be pulled toward the inferior surface of the left ventricle, rather than bending the clip portion 300, inner shaft 452, and inner support catheter 448 outwardly.

This process can be repeated for one or more additional clip portions 300, at least one being attached to another of the heart valve leaflets. After the clip portions 300 have been secured to a respective leaflet, one or more lines of suture 328 (FIG. 9) can be threaded through the coupling members 316 of the clip portions, placed under a desired degree of tension to bring the clip portions together to form an assembly (e.g., the assembly 375) and improve leaflets coaptation, and the free suture ends secured by the locking member 332 (FIG. 9). Alternatively, suture 328 can be pre-threaded thorough the coupling members 316 of the clip portions 300 prior to deployment within the heart. The clip portions 300 can be secured to their respective leaflets as previously described, the suture 324 placed under a desired degree of tension, and the free suture ends secured with the locking member 332. When the clip portions 300 have been appropriately positioned, the actuating connector 456 can be cut or removed, and the delivery assembly 440 removed from the patient.

Although the delivery assemblies 400 and 440 have been described for use with the clip portions 300, they can be used with the leaflet clip assembly 10 in an analogous manner. For example, the actuating connectors 420, 456 can be coupled to a portion of the frames 60 or 68.

Figure 11:
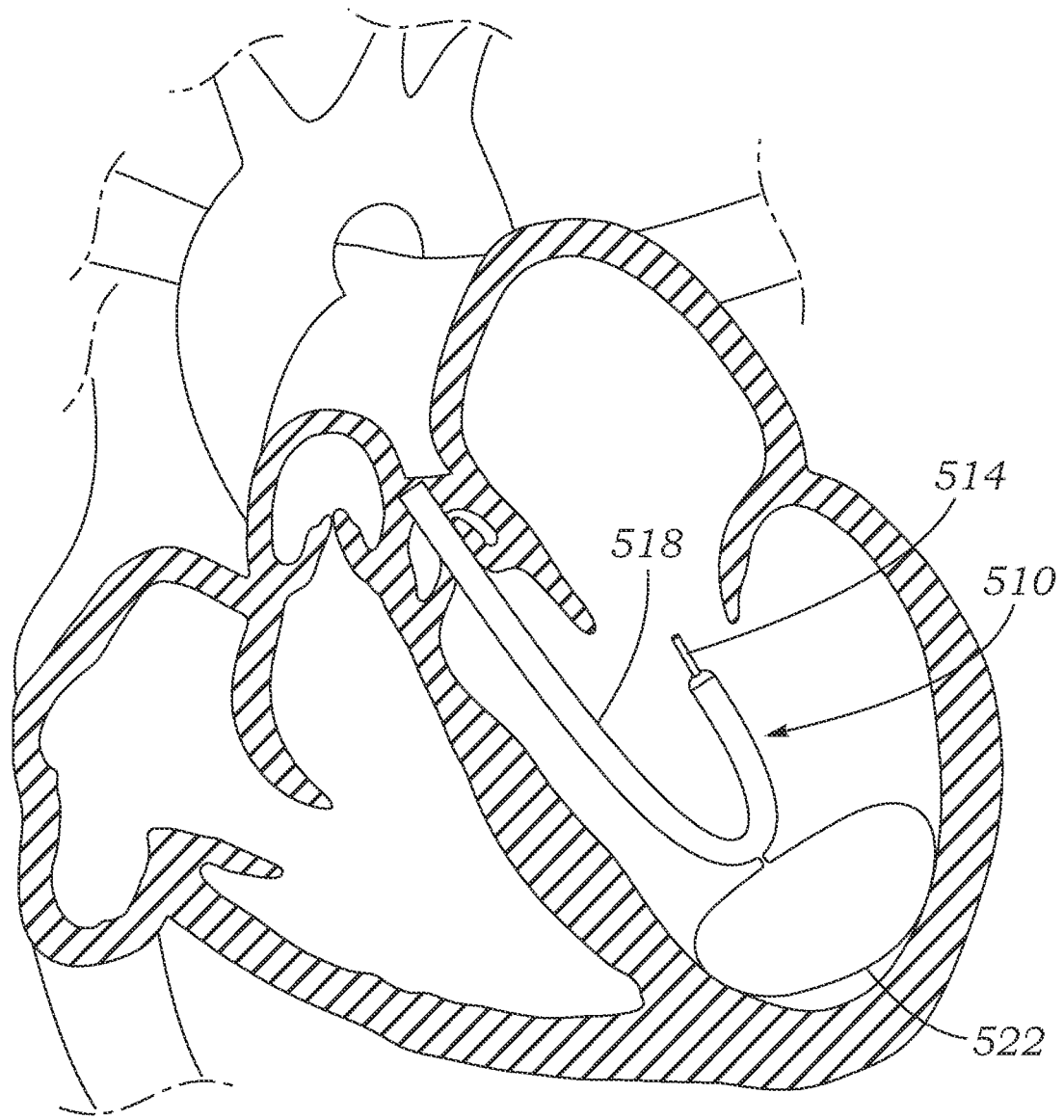
FIG. 11 is a cross section of a heart showing a plurality of catheters inserted into the heart in a retrograde procedure, with a balloon coupled to one of the catheters used to stabilize the catheter in the left ventricular apex zone.

In some aspects, a delivery assembly for delivering and deploying a leaflet repair device, such as the leaflet clip assembly 10 or the clip assembly 375, can include features to help stabilize the delivery assembly at a location within the heart. For example, FIG. 11 illustrates a retrograde deployment procedure where a delivery assembly 510, which can include an inner catheter 514 and an outer catheter 518, has been guided to the left ventricle through the aortic valve. When the outer catheter 518 has been guided to an appropriate position, such as proximate the left ventricular apex zone (e.g., proximate the inferior surfaces of the mitral valve leaflets), a balloon 522 coupled to the outer catheter 518 can be inflated proximate the lower surface of the left ventricle. The balloon 522 can abut the lower ventricular wall, supporting the outer catheter 518 during deployment of a clip portion, such as using the inner catheter 514. In at least some cases, the inner catheter 514 can represent multiple concentric catheters, such as used for delivery of the clip portion 300 using the delivery assembly 400 of FIG. 4.

The repair devices described herein (e.g., leaflet clip assembly 10 or clip assembly 375) have been described in the context of repairing a native mitral valve leaflet. However, it should be understood that disclosed repair devices can be used to repair leaflets of the other native heart valves, or artificial heart valves or artificial heart valve components (e.g., artificial leaflets), including using various transcatheter techniques (e.g., transatrial, transventricular, etc.). The leaflet capture assembly 10 and the clip assembly 375 can, for example, be used to reduce or improve valvular regurgitation by improving coaptation between heart valve leaflets of any of the native heart valves.

As will be further discussed, repair devices can include: (1) one or a plurality of clip portions (e.g., analogous to the clip portion 14 or 18 of the leaflet clip assembly 10, or a clip portion 300) implanted on each leaflet of a heart valve; (2) a single clip portion implanted on multiple leaflets; (3) a single clip assembly of two or more clip portions (e.g., a clip assembly 10 or 375); (4) multiple clip assemblies (e.g., multiple clip assemblies 10 or 375, or a combination of the two); or (5) combinations thereof.

In some cases, a leaflet clip assembly can include a clip portion (e.g., a clip portion 14 or 18 or a clip portion 300)

for each native heart valve leaflet in a valve to be repaired. For example, as shown in FIG. 7, the first leaflet clip portion 14 of the clip assembly 10 can be secured to the anterior mitral valve leaflet and the second leaflet clip portion 18 can be secured to the posterior mitral valve leaflet, with the first and second clip portions being secured to one another after being appropriately positioned so as to improve leaflet coaptation. Similarly, a leaflet clip portion 300 can be secured to the anterior mitral valve leaflet, another leaflet clip portion 300 portion can be secured to the posterior leaflet, and the two leaflet clip portions 300 can be secured to one another to form an assembly after being appropriately positioned so as to improve leaflet coaptation.

In the case of a heart valve with more than two leaflets, such as the tricuspid valve, a leaflet clip assembly (assembly 10 or 375) can include three or more clip portions. For example, when the leaflet clip assembly 10 includes more than two clip portions, a first clip portion can include the base member 30 and additional clip portions can include posts analogous to the second post 42, where the posts can be placed axially on top of one another and axially aligned such that the tension member 38 can extend through lumens of each of the posts, and the base member 30, to secure the clip portions to one another. The clip assembly can be implanted at the center of the native valve such that the clip assembly brings together the three coaptation edges of the leaflets at the center of the native valve. Similarly, at least one clip portion 300 can be secured to each leaflet of the tricuspid valve, and the clip portions can be secured to one another to provide a leaflet clip assembly.

In some cases where a clip assembly is implanted on a native valve having three leaflets, the clip assembly can be implanted on two of the three native leaflets, such as at the commissure defined by the two leaflets. Another clip assembly can be implanted on another pair of leaflets of the same valve, such as at another commissure of the valve.

A leaflet repair device can include more clip portions than leaflets to be secured, including more clip portions than leaflets that are present in a valve to be repaired. In the case of the mitral valve, multiple clip portions can be attached at respective locations along the free edges of the posterior leaflet and the anterior leaflet, and secured together, such as shown above in FIG. 9 for the leaflet clip assembly 375 formed from four clip portions 300. Similarly, for the tricuspid valve, the aortic valve, or the pulmonary valve, one or more clip portions can be implanted on each of the three leaflets of the native valve, with each clip portion being secured to a clip portion of an opposing leaflet, and at least one leaflet secured to more than one clip portion.

In further aspects, at least one clip portion (e.g., clip portion 14, 18, or 300) can be secured to multiple leaflets, which, for example, can allow for fewer clip portions to be used than a number of leaflets to be secured. For example, portions of two leaflets can be secured between the inner and outer frame members of a single clip portion (such as the inner and outer frame members 308, 312, respectively, of clip portion 300). In some implementations, only a single clip portion can be implanted to improve coaptation between two leaflets. In some implementations, multiple clip portions can be secured at respective locations along the coaptation line of two leaflets, with each clip portion receiving opposing edge portions of two leaflets. In such implementations, the individual clip portions can, but need not, be secured to each other. In some cases, having clip portions span multiple leaflets can allow fewer clip portions to be used than a number of leaflets associated with a valve, or can allow for asymmetric valve repair, which can be useful when regurgitation is caused by asymmetric leaflet misalignment.

In one specific implementation, for example, a single clip portion can be secured to both the posterior and anterior leaflets of the native mitral valve such that opposing edge portions of the native leaflets are captured between opposing frame members of the clip portion (e.g., between first frame member 308 and second frame member 312 where the clip portion 300 is used). The clip portion can be placed at any location along the coaptation line of the leaflets (e.g., adjacent a commissure or at any location between the commissures). In the case where two opposing edge portions of leaflets are captured between the opposing frame members of a single clip portion, the single clip portion itself functions as a leaflet repair device. In at least some cases, a single clip portion secured to at least two leaflets can be used to improve leaflet coaptation, and can thus function as a leaflet repair device without being secured to additional clip portions.

Although the present disclosure generally describes the implantation of a single clip assembly to repair a heart valve, multiple clip assemblies can be implanted in a single valve to improve valve function. For example, multiple clip assemblies 10 or 375 may be attached to the posterior and anterior mitral valve leaflets at poorly coapting regions, which may more effectively reduce regurgitation than using a single clip assembly at a single location. Each clip assembly 10 or 375 can include the same or different number of clip portions and can be spaced apart from each other along the coaptation line of the two leaflets. In the case of the tricuspid valve, or another valve with more than two leaflets, multiple clip assemblies 10 or 375 can be attached to two or more leaflets, where each clip assembly can include the same or different numbers of clip portions and can be spaced apart from each other.

In use, a delivery system (such as a delivery system including a delivery device that includes a delivery catheter and a deployment catheter disposed within the delivery catheter) can be introduced into a patient's vasculature (e.g., via the femoral artery or other suitable access point) and percutaneously advanced to the patient's heart using any of various delivery techniques. In a transfemoral procedure, the delivery device can be inserted through a femoral artery and the aorta to the heart in a retrograde direction (typically, but not exclusively used for deploying one or more clip portions on the leaflets of the aortic or mitral valves). Similarly, the delivery device can be inserted through a femoral vein and the vena cava to the right side of the heart in an antegrade direction (typically, but not exclusively used for deploying one or more clip portions on the leaflets of the pulmonary or tricuspid valves). In a transventricular procedure, the delivery device can be inserted through a surgical incision made in the chest and on the bare spot on the lower anterior ventricle wall (typically, but not exclusively used for deploying one or more clip portions on the leaflets of the aortic or mitral valves). Similarly, the delivery device can be inserted through a surgical incision on the wall of the right ventricle to access the pulmonary or tricuspid valves. In a transatrial procedure, the delivery device can be inserted through a surgical incision made in the wall of the left or right atrium to access the native valves on the left or right sides, respectively, of the heart. In a transaortic procedure, the delivery device can be inserted through a surgical incision made in the ascending aorta and advanced toward the heart (typically, but not exclusively used deploying one or more clip portions on the leaflets of the aortic or mitral valves). In a trans-septal procedure, the delivery device can be advanced to the right atrium, such as via a femoral vein, and through the septum separating the right and left ventricles (typically, but not exclusively used for deploying one or more clip portions on the leaflets of the aortic or mitral valves). Further details of delivery techniques for accessing the native valves of the heart are disclosed in U.S. Patent Publication No. 2014/0067052, which is incorporated herein by reference.

It should be noted that the positioning of the disclosed devices (e.g., leaflet clip assembly 10, leaflet clip assembly 375, or components thereof) can be confirmed visually using imaging modalities such as fluoroscopy, X-ray, CT, and MR imaging. Echocardiography in either 2D or 3D can also be used to help guide the positioning of the device.

General Considerations

For purposes of this description, certain aspects, advantages, and novel features of the embodiments of this disclosure are described herein. The disclosed methods, apparatuses, and systems should not be construed as limiting in any way. Instead, the present disclosure is directed toward all novel and nonobvious features and aspects of the various disclosed embodiments, alone and in various combinations and sub-combinations with one another. The methods, apparatuses, and systems are not limited to any specific aspect or feature or combination thereof, nor do the disclosed embodiments require that any one or more specific advantages be present or problems be solved.

Features, integers, characteristics, compounds, chemical moieties, or groups described in conjunction with a particular aspect, embodiment or example of the invention are to be understood to be applicable to any other aspect, embodiment or example described herein unless incompatible therewith. All of the features disclosed in this specification (including any accompanying claims, abstract, and drawings), and/or all of the steps of any method or process so disclosed, may be combined in any combination, except combinations where at least some of such features and/or steps are mutually exclusive. The present disclosure is not restricted to the details of any foregoing embodiments. The present disclosure extends to any novel one, or any novel combination, of the features disclosed in this specification (including any accompanying claims, abstract, and drawings), or to any novel one, or any novel combination, of the steps of any method or process so disclosed.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods.

As used herein, the terms "a", "an" and "at least one" encompass one or more of the specified element. That is, if two of a particular element are present, one of these elements is also present and thus "an" element is present. The terms "a plurality of" and "plural" mean two or more of the specified element.

As used herein, the term "and/or" used between the last two of a list of elements means any one or more of the listed elements. For example, the phrase "A, B, and/or C" means "A," "B," "C," "A and B," "A and C," "B and C" or "A, B and C."

As used herein, the term "coupled" generally means physically coupled or linked and does not exclude the presence of intermediate elements between the coupled items absent specific contrary language.

As used herein, the term "proximal" refers to a position, direction, or portion of a device that is closer to the user and further away from the implantation site. As used herein, the term "distal" refers to a position, direction, or portion of a device that is further away from the user and closer to the implantation site. Thus, for example, proximal motion of a device is motion of the device toward the user, while distal motion of a device is motion of the device away from the user. The terms "longitudinal" and "axial" refer to an axis extending in the proximal and distal directions, unless otherwise expressly defined.

As used herein, the terms "integrally formed" and "unitary construction" refer to a construction that does not include any welds, fasteners, or other means for securing separately formed pieces of material to each other.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. I therefore claim as my invention all that comes within the scope and spirit of these claims.

I claim:

1. A heart valve coaptation device configured to be delivered by a catheter comprising:
    a clip configured to independently capture only a single leaflet of a native heart valve, be released from the catheter and remain attached to the single leaflet when the catheter is withdrawn, the clip comprising:
        an inner frame member comprising curved support frame members, wherein the inner frame member is configured to be positioned on an atrial side of the leaflet of the heart valve;
        a biocompatible covering disposed over the inner frame member to increase a surface area of the curved support frame members;
        an outer frame member coupled to the inner frame member, wherein the outer frame member has a leaflet engagement portion that is configured to be positioned on a ventricular side of the leaflet of the heart valve;
    an actuating connector comprising a flexible piece of material coupled to the leaflet engagement portion of the outer frame member;
    wherein applying tension to the flexible piece of material pulls the leaflet engagement portion of the outer frame member distally to form an opening between the leaflet engagement portion of the outer frame member and the inner frame member that is configured to accept the leaflet of the heart valve; and
    wherein the outer frame member is configured such that releasing the tension on the flexible piece of material causes the leaflet engagement portion of the outer frame member to move proximally and close such that the leaflet of the heart valve is captured between the inner frame member and the leaflet engagement portion of the outer frame member with the inner frame member on the atrial side of the leaflet of the heart valve and the leaflet engagement portion of the outer frame member on the ventricular side of the leaflet.

2. The device of claim 1 further comprising a coupling member attached to the inner frame member.

3. The device of claim 1 further comprising barbs extending from the leaflet engagement portion of the outer frame member.

4. The device of claim 1 wherein the flexible piece of material of the actuating connector comprises a suture.

5. The device of claim 1 wherein applying tension to the flexible piece of material while the inner frame member and the outer frame member are entirely outside the catheter pulls the leaflet engagement portion of the outer frame member distally to form the opening between the leaflet engagement portion of the outer frame member and the inner frame member.

6. The device of claim 1 wherein the clip is configured such that it can form only one opening configured to accept a leaflet of the heart valve.

7. The device of claim 1 wherein the clip comprises only one outer frame member.

8. An assembly comprising:
a heart valve coaptation device comprising a clip configured to independently capture only a single leaflet of a native heart valve, be released from the catheter and remain attached to the single leaflet when the catheter is withdrawn, the clip comprising:
an inner frame member comprising curved support frame members, wherein the inner frame member is configured to be positioned on an atrial side of the leaflet of the heart valve;
a biocompatible covering disposed over the inner frame member to increase a surface area of the curved support frame members;
an outer frame member coupled to the inner frame member, wherein the outer frame member has a leaflet engagement portion is configured to be positioned on a ventricular side of the leaflet of the heart valve;
a catheter releasably coupled to the inner frame member;
an actuating connector comprising a flexible piece of material attached to the leaflet engagement portion of outer frame member;
wherein applying tension to the flexible piece of material of the actuating connector pulls the leaflet engagement portion of the outer frame member distally to form an opening between the leaflet engagement portion of the outer frame member and the inner frame member that is configured to accept the leaflet of the heart valve; and
wherein releasing the tension on the flexible piece of material of the actuating connector allows resiliency of the outer frame member to move the leaflet engagement portion of the outer frame member proximally and close and thereby capture the leaflet of the heart valve between the inner frame member and the leaflet engagement portion of the outer frame member with the inner frame member on the atrial side of the leaflet of the heart valve and the leaflet engagement portion of the outer frame member on the ventricular side of the leaflet.

9. The assembly of claim 8 wherein the flexible piece of material of the actuating connector comprises a suture.

10. The assembly of claim 8 wherein the tension is applied to the actuating connector by a rod.

11. The assembly of claim 8 further comprising a coupling member attached to the inner frame member.

12. The assembly of claim 8 further comprising barbs extending from the leaflet engagement portion of the outer frame member.

13. The assembly of claim 8 wherein the inner frame member comprises a pair of elongate support frame members.

14. The assembly of claim 8 wherein the clip is configured such that it can form only one opening configured to accept a leaflet of the heart valve.

15. An assembly comprising:
a heart valve coaptation device comprising a clip configured to independently capture only a single leaflet of a native heart valve, be released from the catheter and remain attached to the single leaflet when the catheter is withdrawn, the clip comprising:
a metal inner frame member comprising curved support frame members, wherein the metal inner frame member is configured to be positioned on an atrial side of a leaflet of a heart valve;
a fabric covering disposed over the single metal inner frame member to increase a surface area of the curved support frame members;
a metal outer frame member coupled to the metal inner frame member, wherein the metal outer frame member comprises a barbed leaflet engagement portion, wherein the barbed leaflet engagement portion of the metal outer frame member is configured to be positioned on a ventricular side of the leaflet of the heart valve;
a catheter releasably coupled to the metal inner frame member;
an actuating suture attached to the barbed leaflet engagement portion of the metal outer frame member;
wherein applying tension to the actuating suture pulls the barbed leaflet engagement portion of the metal outer frame member distally to form an opening between the barbed leaflet engagement portion of the metal outer frame member and the metal inner frame member that is configured to accept the leaflet of the heart valve between the barbed leaflet engagement portion of the metal outer frame member and the metal inner frame member; and
wherein releasing the tension of the actuating suture allows resiliency of the metal outer frame member to move the barbed leaflet engagement portion of the metal outer frame member proximally and close the barbed leaflet engagement portion of the metal outer frame member and thereby capture the leaflet of the heart valve between the metal inner frame member and the barbed leaflet engagement portion of the metal outer frame member with the metal inner frame member on the atrial side of the leaflet of the heart valve and the barbed leaflet engagement portion of the metal outer frame member on the ventricular side of the leaflet.

16. The assembly of claim 15 wherein the tension is applied to the actuating suture by a rod.

17. The assembly of claim 15 further comprising a coupling member attached to the metal inner frame member.

18. The assembly of claim 15 wherein the metal inner frame member comprises a pair of elongate support frame members.

19. The assembly of claim 15 wherein the metal inner frame member has a convex shape.

20. The assembly of claim 15 wherein the clip comprises only one outer frame member.

* * * * *